(12) United States Patent
Warriner et al.

(10) Patent No.: US 11,932,897 B2
(45) Date of Patent: Mar. 19, 2024

(54) BIOSYNTHESIS OF CURCUMINOIDS IN MAMMALIAN CELLS

(71) Applicant: University of Kentucky Research Foundation, Lexington, KY (US)

(72) Inventors: Logan W. Warriner, Lexington, KY (US); Daniel W. Pack, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 747 days.

(21) Appl. No.: 16/719,843

(22) Filed: Dec. 18, 2019

(65) Prior Publication Data

US 2020/0199630 A1 Jun. 25, 2020

Related U.S. Application Data

(60) Provisional application No. 62/781,343, filed on Dec. 18, 2018.

(51) Int. Cl.

| | |
|---|---|
| *C12P 7/26* | (2006.01) |
| *A61K 35/22* | (2015.01) |
| *A61K 48/00* | (2006.01) |
| *C12N 5/071* | (2010.01) |
| *C12N 5/10* | (2006.01) |
| *C12N 9/22* | (2006.01) |
| *C12N 15/11* | (2006.01) |
| *C12N 15/85* | (2006.01) |

(52) U.S. Cl.
CPC .............. *C12P 7/26* (2013.01); *A61K 35/22* (2013.01); *C12N 5/0686* (2013.01); *C12N 5/10* (2013.01); *C12N 9/22* (2013.01); *C12N 15/11* (2013.01); *C12N 15/85* (2013.01); *A61K 48/00* (2013.01); *C12N 2310/20* (2017.05); *C12N 2510/00* (2013.01); *C12N 2800/80* (2013.01); *C12Y 114/14* (2013.01); *C12Y 201/01104* (2013.01); *C12Y 203/01* (2013.01); *C12Y 403/01023* (2013.01); *C12Y 602/01012* (2013.01); *C12Y 604/01002* (2013.01)

(58) Field of Classification Search
None
See application file for complete search history.

(56) References Cited

PUBLICATIONS

Yohei Katsuyama Production of curcuminoids by *Escherichia coli* carrying an artificial biosynthesis pathway (Year: 2008).*
Genes and Enzymes Involved in Caffeic Acid Biosynthesis Journal of Bacteriology, Apr. 2006, p. 2666-2673 vol. 188, No. 7 (Year: 2006).*
Yansheng Zhang et al Using Unnatural Protein Fusions to Engineer Resveratrol Biosynthesis in Yeast and Mammalian Cells J. Am. Chem. Soc. 2006, 128, 13030-13031 (Year: 2006).*
Rodrigues et al., Heterologous Production of Curcuminoids, Microbiol. Mol. Biol. Rev. 79, 2015, 39-60. (Year: 2015).*
Fang, Z., Jones, J. A., Zhou, J., & Koffas, M. A. (2018). Engineering *Escherichia coli* Co-Cultures for Production of Curcuminoids From Glucose. Biotechnology journal, 13(5), 1700576.
Katsuyama, Y., Matsuzawa, M., Funa, N., & Horinouchi, S. (2007). In vitro synthesis of curcuminoids by type III polyketide synthase from *Oryza sativa*. Journal of Biological Chemistry.
Katsuyama, Y., Matsuzawa, M., Funa, N., Horinouch, S. (2008) Production of curcuminoids by *Escherichia coli* carrying an artificial biosynthesis pathway, Microbiology-Sgm, 154: 2620-2628.
Rodrigues, J. L., Araujo, R. G., Prather, K. L., Kluskens, L. D., & Rodrigues, L. R. (2015). Production of curcuminoids from tyrosine by a metabolically engineered *Escherichia coli* using caffeic acid as an intermediate. Biotechnology journal, 10(4), 599-609.
Rodrigues, J.L., Prather, K.L.J., Kluskens, L.D., Rodrigues, L.R. (2015) Heterologous Production of Curcuminoids, Microbiology and Molecular Biology Reviews, 79: 39-60.

* cited by examiner

*Primary Examiner* — Todd M Epstein
(74) *Attorney, Agent, or Firm* — Stites & Harbison PLLC; Mandy Wilson Decker

(57) ABSTRACT

A method of making curcuminoids in a mammalian cell. The method of making a curcuminoid in a mammalian cell includes expressing one or more enzymes in the mammalian cell, the enzymes being selected from the group consisting of tyrosine ammonia lyase (TAL), 4-coumaroyl-CoA ligase (4CL1), curcuminoid synthase (CUS), diketide-CoA synthase (DCS), curcumin synthase (CURS1), 4-coumarate 3-hydroxylase (C3H), caffeoyl-CoA 3-O-methyltransferase (CCoAMT), and acetyl-CoA carboxylase (ACC). The expressing of the one or more enzymes converts a starting material, such as tyrosine or ferulic acid, to the curcuminoid. Also provided herein are therapeutic uses for the curcuminoid made in a mammalian cell.

19 Claims, 10 Drawing Sheets
Specification includes a Sequence Listing.

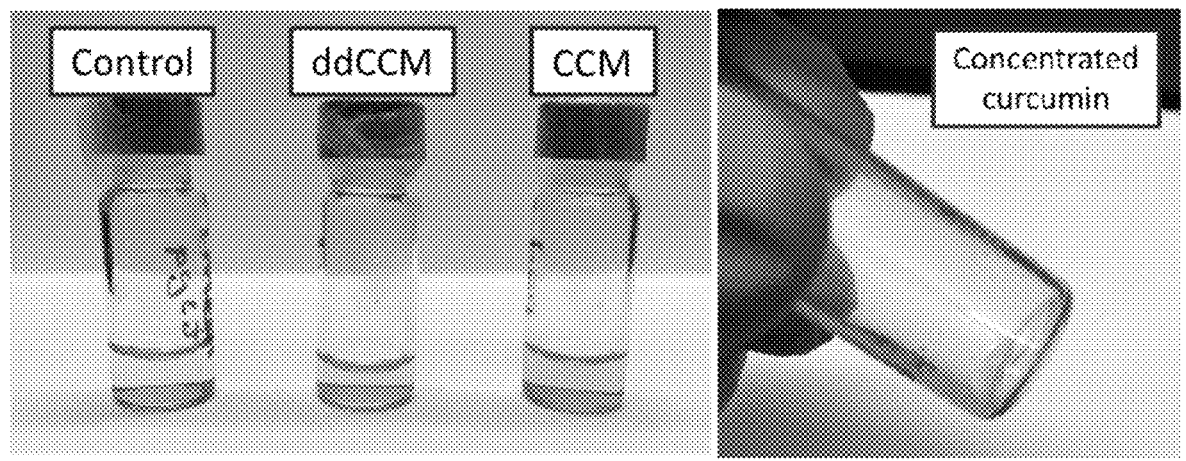
FIG. 5A
FIG. 5B
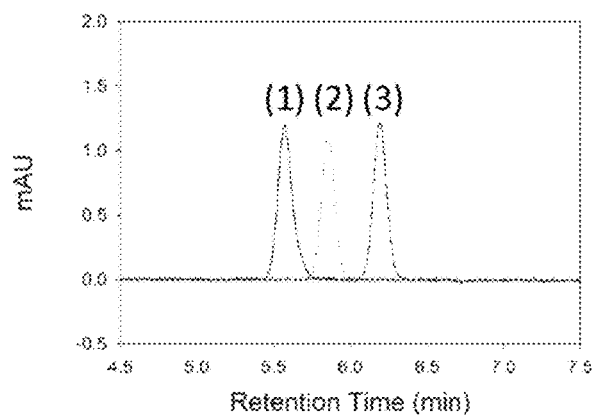
FIG. 5C
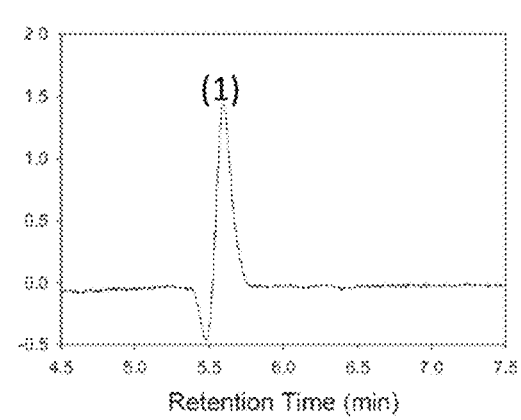
FIG. 5D

SEQUENCE LISTING

<160> NUMBER OF SEQ ID NOS: 3

<210> SEQ ID NO 1
<211> LENGTH: 60
<212> TYPE: DNA
<213> ORGANISM: Rhodotorula glutinis

<400> SEQUENCE: 1
atggctccgc gtccgacctc gcaatcccaa gctcgcacct gcccgaccac ccaagttacc    60

<210> SEQ ID NO 2
<211> LENGTH: 60
<212> TYPE: DNA
<213> ORGANISM: Artificial Sequence

```
<220> FEATURE:
<223> OTHER INFORMATION: Human codon optimized sequence for TAL
      predicted by GeneOptimizer

<400> SEQUENCE: 2
atggctccca ggccgacttc acagagtcag gccagaacgt gtccaacgac acaagtgacc      60

<210> SEQ ID NO 3
<211> LENGTH: 60
<212> TYPE: DNA
<213> ORGANISM: Artificial Sequence
<220> FEATURE:
<223> OTHER INFORMATION: Preferred human codon optimized sequence for
      TAL

<400> SEQUENCE: 3
atggccccca gacccaccag ccagagccag gccagaacct gccccaccac ccaggtgacc      60
```

BIOSYNTHESIS OF CURCUMINOIDS IN MAMMALIAN CELLS

RELATED APPLICATIONS

This application claims the benefit of U.S. Provisional Application Ser. No. 62/781,343, filed Dec. 18, 2018, the entire disclosure of which is incorporated herein by this reference.

GOVERNMENT INTEREST

This invention was made with government support under grant number GF-18-025 awarded by the NASA Kentucky Space Grant Consortium. The government has certain rights in the invention.

SEQUENCE LISTING

The instant application contains a Sequence Listing which has been submitted in ASCII format via EFS-Web and is hereby incorporated by reference in its entirety. The ASCII copy of the Sequence Listing, which was created on Dec. 18, 2019, is named 13177N-2292US_ST25.txt and is 1 kilobyte in size.

TECHNICAL FIELD

The presently-disclosed subject matter generally relates to production of curcuminoids. In particular, certain embodiments of the presently-disclosed subject matter relate to production of curcuminoids in mammalian cells and related therapeutic uses.

BACKGROUND

Ionizing radiation travels through living tissues, depositing energy that causes structural damage to DNA and alters many cellular processes. Once astronauts venture beyond Earth's protective atmosphere, they may be exposed to the high energy charged particles of galactic cosmic rays and solar particle events (SPE), as well as secondary protons and neutrons. However, because the ionization patterns of these particles in biomolecules, cells, and tissues are distinct from terrestrial radiation, the resulting effects are poorly understood, and the amount of risk involved is subject to large uncertainties. Despite these uncertainties, exposure to space radiation in long-term missions is estimated to increase the chance of lethal cancer by 5 to 21% (high atomic number, high energy protons (HZE), reactive oxygen species (ROS)).

In view thereof, one of the major goals of NASA's Space Radiation Program Element (SRPE) is to address these uncertainties and develop the knowledge base required to accurately predict and efficiently manage the radiation risk of human spaceflight. With that in mind, NASA has identified the following health concerns as its highest research priorities: A) risk of radiation carcinogenesis from space radiation (e.g., increased risk of cancers); B) risk of acute or late central nervous system effects from space radiation (e.g., changes in motor function and behavior or neurological disorders); C) risk of degenerative tissue or other health effects from space radiation (e.g., other degenerative tissue defects such as cataracts, circulatory diseases, and digestive diseases); and D) acute radiation risks from space radiation (e.g., prodromal risks, significant skin injury, or death from a major solar event or combination solar/galactic cosmic ray event that jeopardizes crew and mission survival).

Because there are no human epidemiological data for these radiation types, risk estimation must be derived from mechanistic understanding based on radiation physics, and on molecular, cellular, tissue, and organismal radiation biology related to cancer, risk to the central nervous system, and other risks of concern to NASA. As such, the current knowledge base has been built over time and continues to be augmented by a peer-reviewed, largely ground-based research program utilizing the NASA Space Radiation Laboratory at the Brookhaven National Laboratory and the Loma Linda University Proton Treatment Center. Experiments performed at these facilities mimic conditions of the space radiation environment and contribute to the development of risk models, a greater knowledge of the genetic consequences of heavy ions to biological systems, and better methods of spacecraft shielding. This NASA sponsored research seeks an understanding of DNA structural and functional changes caused by radiation, basic metabolic controls known to be modulated by radiation, genomic instability, changes to tissue structure, and "bystander" or non-targeted effects. In particular, this research seeks to reduce the uncertainties in risk predictions for cancer and acute radiation risks; and provide the necessary data and knowledge to develop risk projection models for central nervous system (CNS) and other degenerative tissue risks.

Based upon this research, current strategies to reduce radiation exposure include engineering countermeasures (e.g., shielding material, vessel design) and time management (e.g., length of mission, LEO vs. beyond LEO). Notably, there are currently no approved biological countermeasures to mitigate or prevent the detrimental effects of radiation exposure in space. In this regard, it is noted that the three most prevalent curcuminoids (curcumin, demethoxycurcumin, and bisdemethoxycurcumin), which are naturally-occurring diarylheptanoids isolated from the rhizome of the plant *Curcuma Longa*, have recently been studied due to benefits, such as antioxidant, anticancer, antibacterial, anti-inflammatory, and anti-Alzheimer's properties (FIG. 1). However, clinical success of curcumin treatment remains to be realized, primarily due to the poor bioavailability of curcumin in vivo. More specifically, curcumin suffers from poor solubility in aqueous environments, rapid metabolism, and prompt clearance by the kidneys, which result in oral bioavailability of as little as 1% and only slightly increased availability through intravenous administration.

Accordingly, there remains a need for a biological countermeasure to mitigate or prevent the detrimental effects of radiation exposure in space.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method of making a curcuminoid in a mammalian cell, the method comprising expressing one or more enzymes in the mammalian cell, the enzymes being selected from the group consisting of tyrosine ammonia lyase (TAL), 4-coumaroyl-CoA ligase (4CL1), curcuminoid synthase (CUS), diketide-CoA synthase (DCS), curcumin synthase (CURS1), 4-coumarate 3-hydroxylase (C3H), caffeoyl-CoA 3-O-methyltransferase (CCoAMT), and acetyl-CoA carboxylase (ACC); wherein the expressing the one or more enzymes convert a starting material to the curcuminoid. In some embodiments, the starting material is ferulic acid. In one embodiment, the one or more enzymes are 4CL1 and CUS. In another embodiment, the curcuminoid is one or more of curcumin and demethoxycurcumin.

In some embodiments, the starting material is tyrosine. In one embodiment, the one or more enzymes are TAL, 4CL1, and CUS. In another embodiment, the curcuminoid is bisdemethoxycurcumin. In one embodiment, the one or more enzymes are TAL, C3H, 4CL1, CCoAOMT, and CUS or CURS1 and DCS. In another embodiment, the one or more enzymes are TAL, C3H, 4CL1, CCoAOMT, and CUS. In another embodiment, the one or more enzymes are TAL, C3H, 4CL1, CCoAOMT, CURS1, and DCS. In another embodiment, the curcuminoid is one or more of curcumin, demethoxycurcumin, and bisdemethoxycurcumin.

In some embodiments, the method includes, prior to expressing the one or more enzymes, delivering genetic material of the one or more enzymes to the mammalian cell. In some embodiments, the genetic material is delivered via polymer-DNA, a viral system, or clustered regularly interspaced short palindromic repeats (CRISPR)/CRISPR-associated protein-9 (Cas9) system. In one embodiment, the polymer-DNA delivery includes modified polyethylenimine (PEI) polymer. In one embodiment, the CRISPR/Cas9 system includes simultaneous insertion of up to six genes at a single locus. In some embodiments, delivering the genetic material includes delivering a different concentration of genetic material for at least one of the one or more enzymes. In some embodiments, the method further includes providing malonyl-CoA to the cell. In one embodiment, providing the malonyl-CoA to the cell includes expressing ACC in the cell.

Also provided herein, in some embodiments, is a method of delivering a curcuminoid for therapeutic use, the method comprising making a curcuminoid in a mammalian cell. In one embodiment, the method includes at least one of delivering genetic material corresponding to the one or more enzymes to the cell in vivo; harvesting the cell from a subject, delivering the genetic material corresponding to the one or more enzymes to the cell in vitro, and reimplanting the cell; or harvesting the cell from a subject, delivering the genetic material corresponding to the one or more enzymes to the cell in vitro, encapsulating the cell, and administering the encapsulated cell to the subject in a tissue cage.

Further features and advantages of the presently-disclosed subject matter will become evident to those of ordinary skill in the art after a study of the description, figures, and non-limiting examples in this document.

BRIEF DESCRIPTION OF THE DRAWINGS

FIGS. 5A-D show images and graphs illustrating production and quantification of curcuminoid-producing cells. (A) Cell media from curcuminoid-producing cells generated by polymer-mediated transfection of HEK293 cells. (B) Curcumin solution resulting from ethyl acetate extraction of CCM from cell media and subsequent concentration by evaporation. (C) HPLC traces of ddCCM (1), dCCM (2), and CCM (3) standards. (D) HPLC of ddCCM extracted from HEK293 cell media.

DESCRIPTION OF EXEMPLARY EMBODIMENTS

Figure 1:
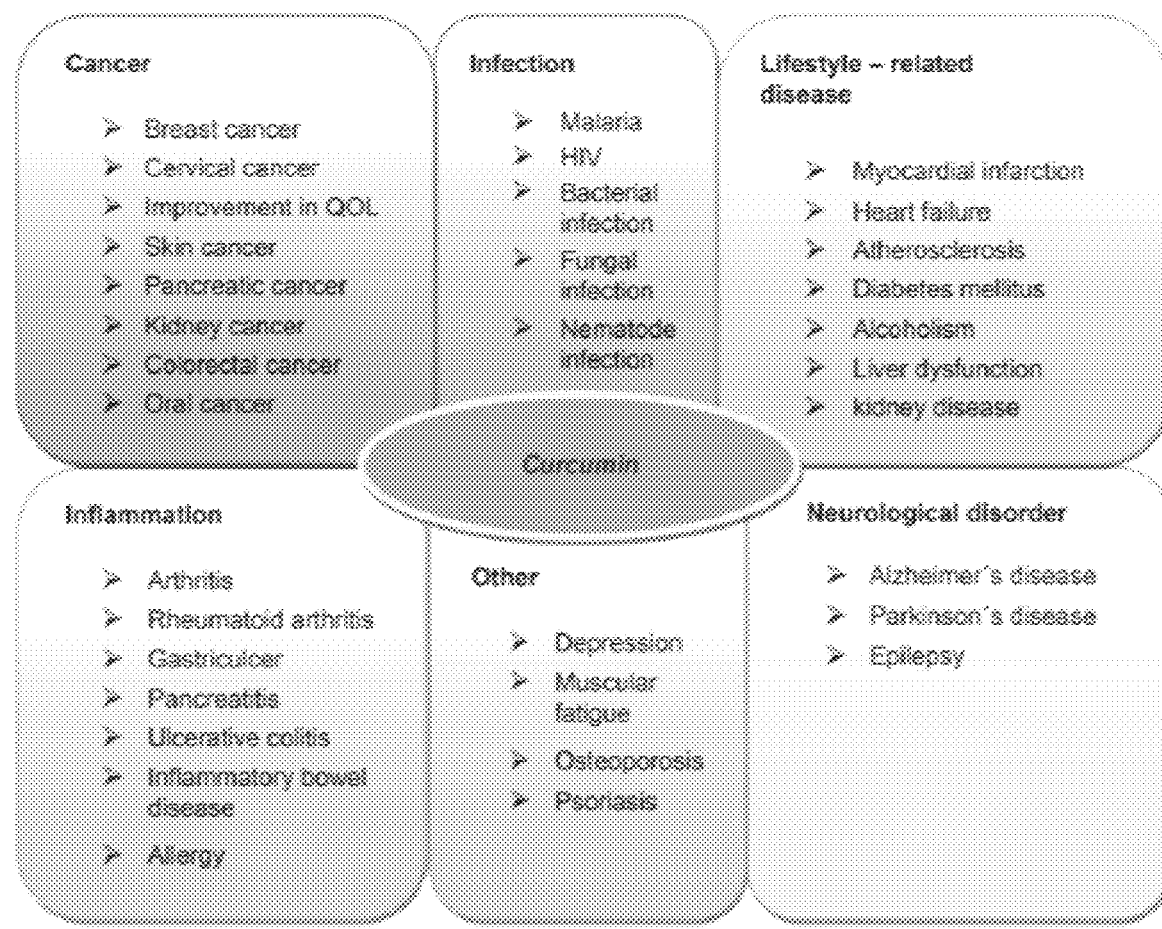
FIG. 1 shows an image summarizing conditions in which curcuminoids have been studied for therapeutic effects.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter relates to curcuminoids, and the production and use thereof. In some embodiments, the disclosure relates to a method of making curcuminoids in a mammalian cell. For example, in some embodiments, the method of making a curcuminoid in a mammalian cell includes expressing one or more enzymes in the mammalian cell and, through the expression of the one or more enzymes, producing one or more curcuminoids from a starting material. The starting material includes any suitable material, such as, but not limited to, ferulic acid, naturally-occurring tyrosine, p-coumaric acid, or supplemented cinnamic acids. In one embodiment, the one or more enzymes include, but are not limited to, tyrosine ammonia lyase (TAL), 4-coumaroyl-CoA ligase (4CL1), curcuminoid synthase (CUS), diketide-CoA synthase (DCS), curcumin synthase (CURS1), 4-coumarate 3-hydroxylase (C3H), caffeoyl-CoA 3-O-methyltransferase (CCoAMT), acetyl-CoA carboxylase (ACC), or combinations thereof. In another embodiment, the method involves expressing, in the mammalian cell, at least 2 enzymes, at least 3 enzymes, between 2 and 7 enzymes, between 2 and 6 enzymes, between 2 and 5 enzymes, between 3 and 7 enzymes, between 3 and 6 enzymes, between 3 and 5 enzymes, or any combination, sub-combination, range, or sub-range thereof.

Figure 2:
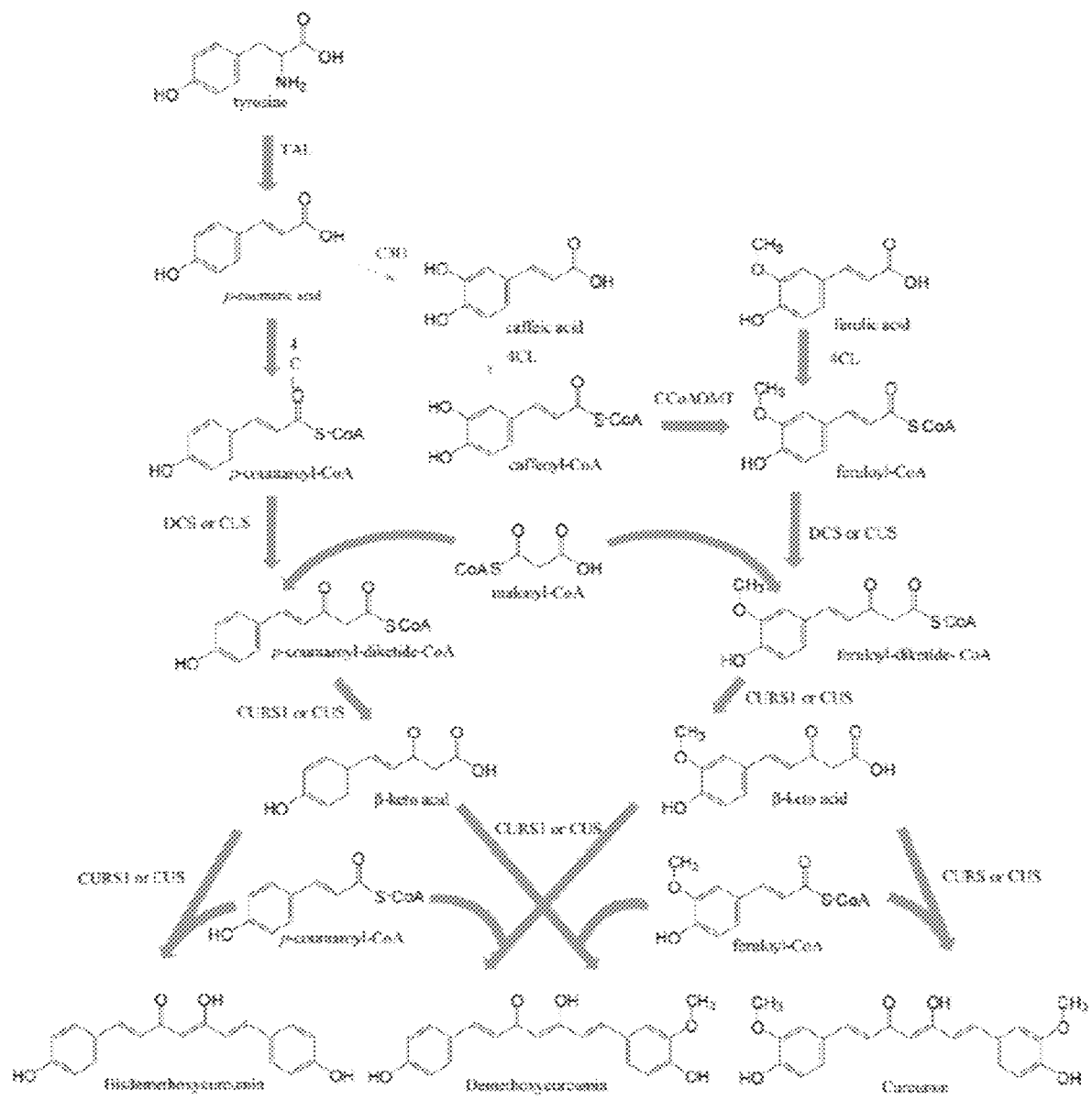
FIG. 2 shows a schematic illustrating a biosynthetic pathway for the production of curcuminoids from tyrosine and cinnamic acid substrates. TAL: tyrosine ammonia lyase; C3H: 4-coumarate-3-hydroxylase; 4CL: 4-coumarate-CoA ligase; CCoAOMT: caffeoyl-CoA 3-0 methyltransferase; DCS: diketide-CoA synthase; CURS1: curcumin synthase; and CUS: curcuminoid synthase.

Referring to FIG. 2, in some embodiments, the method includes expressing at least 4CL1 and CUS in mammalian cells, where 4CL1 conjugates coenzyme factor A (CoA) to a precursor/intermediate in the curcuminoid synthesis pathway and CUS catalyzes a multi-step reaction that converts the CoA conjugated precursor/intermediate to a curcuminoid. For example, in some embodiments, the method of making a curcuminoid includes directly converting ferulic acid to curcumin (CM) and/or demethoxycurcumin (dCCM) through expression of 4CL1 and CUS. In some embodiments, the method includes first converting tyrosine to the precursor/intermediate p-coumaric acid through expression of TAL. In one embodiment, after converting tyrosine to p-coumaric acid, 4CL1 adds a coenzyme factor A (CoA) unit to the p-coumaric acid to form p-coumaroyl-CoA, and CUS catalyzes a multi-step reaction that converts the p-coumaroyl-CoA to bisdemethoxycurcumin (ddCCM). In one embodiment, after converting tyrosine to p-coumaric acid, C3H converts p-coumaric acid to cinnamic acid, 4CL1 adds a CoA unit to the cinnamic acid to form caffeoyl-CoA, CCoAOMT converts caffeoyl-CoA to feruloyl-CoA, and CUS catalyzes a multi-step reaction that converts the cinnamoyl-CoA structure to a curcuminoid. Additionally or alternatively, in some embodiments, CUS may be replaced by DCS and CURS1 to catalyzes the conversion of the precursor/intermediate to a curcuminoid.

In some embodiments, the amount of each cinnamoyl-CoA structure shifts and/or determines the curcuminoid product being formed. For example, in one embodiment, feruloyl-CoA favors the production of curcumin, caffeoyl-CoA favors the production of dCCM, and p-coumaroyl-CoA favors the production of ddCCM. By tuning the prevalence of each CoA structure through the supplementation of media with intermediates, or by altering the expression of certain genes, both the concentration of, and the specific curcuminoid, are controlled. This favored product is further controlled by using different curcuminoid synthases, CUS or DCS/CURS1. CUS catalyzes reactions that favor the production of bisdemethoxycurcumin, while the allosteric regulating pair DCS and CURS1 catalyze reactions that favor curcumin.

Additionally or alternatively, in some embodiments, the amount of malonyl-CoA is a limiting factor in the synthesis of curcuminoids. For example, in one embodiment, 1 mole of malonyl-CoA=1 mole of curcuminoid. The malonyl-CoA may be provided by any suitable method depending upon the environment in which the curcuminoids are being synthesized. In some embodiments, where the curcuminoids are synthesized in vivo, the malonyl-CoA is provided from a native cellular pool and/or is supplemented. In some embodiments, the amount of native malonyl-CoA is increased through overexpression of acetyl-CoA carboxylase (ACC), such as, for example, by delivering an ACC-encoding plasmid to the cell. In some embodiments, where the curcuminoids are synthesized in vitro, the growth media is supplemented with malonate, disodium malonate, and/or malonyl-CoA.

The one or more enzymes may be expressed in the mammalian cell through any suitable method. In some embodiments, the one or more enzymes are expressed through delivery of genetic material via polymer-DNA. For example, in some embodiments, the biosynthetic pathway of the one or more enzymes is produced within the cell through the delivery of plasmid DNA(s) encoding for the one or more enzymes using a modified polyethylenimine (PEI) polymer. In one embodiment, the modified PEI polymer is used to deliver one or more plasmid DNAs (pDNA) encoding for one or more of the enzymes disclosed herein. In another embodiment, the one or more enzymes include, but are not limited to, TAL, 4CL1, CUS, DCS, CURS1, C3H, CCoAMT, ACC, or a combination thereof. In another embodiment, the modified PEI polymer is used to deliver the one or more plasmid DNAs to human cells. In a further embodiment, the encoded enzymes are produced by the transfected mammalian cells within about 4 hours of the delivery, or transfection, of the genetic material.

Additionally or alternatively, in some embodiments, the one or more enzymes are expressed through delivery of genetic material via viral or clustered regularly interspaced short palindromic repeats (CRISPR)/CRISPR-associated protein-9 (Cas9) systems. In some embodiments, the delivery of genetic material via viral or CRISPR/Cas9 system provides an increase in the number of cells expressing the enzymes, and thus the number of cells producing curcuminoids, as compared to the polymer-DNA delivery. For example, in one embodiment, the delivery of genetic material via viral or CRISPR/Cas9 systems provides a 10- to 100-fold increase in curcuminoid production levels, as compared to the polymer-DNA delivery. In some embodiments, the CRISPR/Cas9 system includes simultaneous insertion of up to six genes at a single locus. In some embodiments, the viral system includes delivery with lentiviral vectors.

In some embodiments, the method of making curcuminoids in mammalian cells, or the biosynthesis pathway, is at least partially controlled by an antioxidant response element (ARE). For example, in some embodiments, the ARE is coupled to one or more of the enzymes and interacts with one or more elements of oxidative stress to initiate the biosynthesis pathway. In one embodiment, the ARE provides a positive feedback loop, where nuclear factor E2-related factor 2 (Nrf2), the levels of which increase in the presence of ROS or reduction of glutathione, activates curcuminoid biosynthesis through the ARE, which in turn increases expression of Nrf2, driving further production of curcuminoids.

As will be understood by those skilled in the art, the concentration of genetic material and delivery material will vary based upon the specific genetic material being delivered and the delivery method. For example, in some embodiments, the growth media for the mammalian cells includes from 0.5-5 μg/mL of pDNA and from 0.5-20 μg/mL of polymer. Additionally or alternatively, the concentration of genetic material relating to each of the one or more enzymes may vary depending upon the specific enzymes to be expressed. For example, the growth media or delivery composition may include an equal amount of each pDNA (e.g., 1:1 ratio, 1:1:1 ratio, 1:1:1:1 ratio, 1:1:1:1:1 ratio, etc.), or different amounts of at least one pDNA (e.g., 0.5:2 ratio, 1:2 ratio, 0.5:2:1 ratio, etc.), for any combination of DNA being delivered. In some embodiments, genes that are expressed together, such as 4CL1/CUS or DCS/CURS1, may be subcloned into a bicistronic expression vector to provide particular expression levels and reduce the number of plasmids that must be simultaneously transfected.

The amount of curcuminoids being produced at each concentration may be quantified using high-performance liquid chromatography (HPLC). For example, the production of bisdesmethoxycurcumin, desmethoxycurcumin, and curcumin may be quantified using HPLC analysis with retention times of 5, 5.5, and 6 minutes, respectively, a ACN:$H_2O$ ratio of 60:40 to 100:0 at 1 mL/min, and a wavelength of 425 nm. Although described herein primarily with respect to specific methods of delivering genetic material and certain mammalian cells, as will be appreciated by those skilled in the art, the disclosure is not so limited and may include any other suitable method of delivering genetic material to human cells or any other suitable mammalian cell.

The synthesis of curcuminoids in mammalian cells according to one or more of the embodiments disclosed herein provides in situ, local production of curcuminoids. This production in mammalian cells addresses the poor bioavailability of curcumin through existing delivery methods, such as oral or parenteral administration, and circumvents the need for special methods to deliver curcumin (e.g., nanoformulations, conjugations, encapsulation, etc.). Additionally, the presently-disclosed methods are distinct from existing methods using bacteria and, without wishing to be bound by theory, are believed to represent the first ever production of curcuminoids, or any naturally occurring plant-derived biomolecule, in mammalian cells.

By enabling mammalian cells, including human cells, to produce curcumin, focus can be shifted away from the delivery of curcumin, and instead, more attention can be placed on study of the direct therapeutic effects. Applications range anywhere from potential radiation-protective properties for astronauts, to novel cancer treatments and preventions, to treatment of bacterial infections. For example, in some embodiments, the methods of producing curcuminoids disclosed herein provide delivery of the curcuminoids for therapeutic use as anti-oxidants, cancer therapeutics, anti-inflammatories, anti-bacterials, against neurodegenerative diseases, and any other disease or condition for which curcuminoids may be used.

Treatment modalities can include, for example, ex vivo cell therapy and in vivo gene therapy. An ex vivo cell therapy would entail harvesting cells from the patient, in vitro transfection (using retroviral or lentiviral vectors or CRISPR/Cas9), expansion of selected curcumin-producing cells, and reimplantation of cells in the patient. Alternatively, rather than reimplantation, the curcuminoid-producing cells could be encapsulated and administered to a patient in tissue cages. This approach may be preferred for some indications as the cells could be retrieved relatively easily to terminate the therapy at any time. Gene therapy would entail delivery of the curcuminoid biosynthesis gene cluster to the patient's cell in vivo using an appropriate vector, such as a lentiviral or other gene delivery system. In some embodiments, the vector encodes the gene cluster on a single construct. In some embodiments, the vector, such as the lentiviral or other gene delivery system, includes any vector suitable for encoding a construct that is too large to be packed by adeno-associated viral vectors (AVV).

Although described herein primarily with respect to curcuminoids, as will be appreciated by those skilled in the art, the disclosure is not so limited and expressly includes other potentially therapeutic compounds not naturally occurring in humans. These other compounds include, but are not limited to, resveratrol, antioxidant stilbenoids, and flavonoids. In addition, the enzymatic pathways, which may include genetically engineered enzymes, may provide for biosynthesis of other compounds, including those with no natural analogs. That is, the curcuminoid biosynthesis method disclosed herein provides a platform for biosynthesis of other therapeutic compounds, including both compounds that are not naturally occurring in humans and compounds with no natural analogs. These compounds may be synthesized from natural or non-natural starting materials using wild-type and/or engineered enzymes.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Throughout medical history, therapeutic molecules have been isolated from their natural source—primarily plants and microorganisms—or synthesized in a laboratory, formulated for delivery to the patient, and administered through an appropriate route, most commonly orally. Very recently, gene and cell therapies have emerged that provide for the synthesis of a therapeutic protein or nucleic acid within human cells in vivo. These Examples introduce a new medical paradigm in which small-molecule therapeutics, including those not naturally present in human cells, are produced in vivo by the patient's own cells. Also introduced herein are therapeutic approaches based on in-vivo drug biosynthesis that involve metabolic engineering of an enzymatic pathway capable of producing a drug in human cells from naturally occurring starting materials, safe and efficient introduction of the gene cluster to the patient, identification of appropriate promoters for regulation of drug production, and a method to remove or turn off the transformed cells at the termination of therapy.

Turmeric and its extracts have been used as a spice, as a dietary supplement, and in traditional Ayurvedic and Chinese medicine for treatment of asthma, allergies, cough, sinusitis, and hepatic disease. Curcumin was first isolated in the 19$^{th}$ century, and its structure was determined and the compound first synthesized more than 100 years ago. Curcumin (CCM) and its analogs demethoxycurcumin (dCCM) and bisdemethoxycurcumin (ddCCM) are polyphenolic compounds derived from the rhizomes of turmeric, *Curcuma longa*. Curcuminoids are conventionally extracted from dry rhizomes of *C. longa*, and the extract comprises a mixture of CCM (77%), dCCM (18%), and ddCCM (5%). As with most phytochemicals, however, curcuminoids accumulate in low quantities over long growth periods and must be extracted from complex mixtures of chemicals that vary compositionally from batch to batch, making them difficult and expensive to isolate. Thus, interest in development of heterologous production platforms yielding large amounts of single-entity curcuminoids has grown in the past decade.

More recently, researchers have reported the antioxidant, anti-inflammatory, thrombosuppressive, antimicrobial, antidiabetic, and anticancer potential of curcuminoids. The specific mechanisms leading to the diverse therapeutic effects of curcuminoids are beginning to be elucidated. Curcuminoids are most commonly known as potent antioxidants due to scavenging of free radicals by their phenol and ketone moieties. Furthermore, several specific molecular targets have been identified including transcription factors, inflammatory mediators, and protein kinases. For example, the curcuminoids (CCM, dCCM, and ddCCM exhibit similar bioactivity) are known to suppress activation of nuclear factor-κB (NF-κB), inhibit the Notch signaling pathway, inhibit interleukin (IL)-6-induced phosphorylation and nuclear translocation of signal transducer and activator of transcription 3 (STAT3), inhibit activator protein (AP)-1, suppress the Wnt/β-catenin signaling pathway, activate peroxisome proliferator-associated receptor (PPAR)-γ, and upregulate expression of p53. As a result, curcumin has been tested in numerous animal models of cancer, including breast, oral, head and neck, pancreatic, prostate, and colon. In addition, curcumin has been shown to downregulate cytokines including tumor necrosis factor (TNF)-α, IL-1, -6, and -8, and to inhibit expression of proinflammatory cytokines such as inducible nitric oxide synthase (iNOS) and cyclooxygenase (COX)-2. Thus, curcuminoids are being investigated as treatments for a range of disease states including inflammation, ischemia, atherosclerosis, and neurodegenerative diseases.

Despite these efforts, clinical success of curcumin therapies is hindered by a number of factors. Perhaps most importantly, curcuminoids are poorly water soluble (~1 µg/mL) and, as a result, exhibit poor oral absorption and bioavailability, making curcumin a BCS class II drug. In addition, curcumin is rapidly hydrolyzed at physiological pH, rapidly metabolized via glucuronidation, and cleared by renal elimination, leading to a relatively short half-life in plasma. To overcome these limitations, a variety of delivery strategies are being investigated including liposomes, polymer micelles, polymer and lipid nanoparticles, micro- and nanoemulsions, cyclodextrin inclusion complexes, and nanocrystal suspensions.

Biosynthesis of curcuminoids by the patient's cells in vivo, regulated by endogenous signals for the biosynthesis and release of therapeutic amounts of curcuminoids, is believed to circumvent the aforementioned limitations, provide for long-term curcuminoid therapy with a single treatment, and offer a conceptually new approach to drug delivery. These Examples demonstrate the development of such a novel therapy, including engineering of human cells to express a cluster of plant-derived enzymes that catalyze the biosynthesis of curcuminoids from tyrosine. This is believed to be the first synthesis of a plant-derived therapeutic molecule in mammalian cells.

Figure 3:
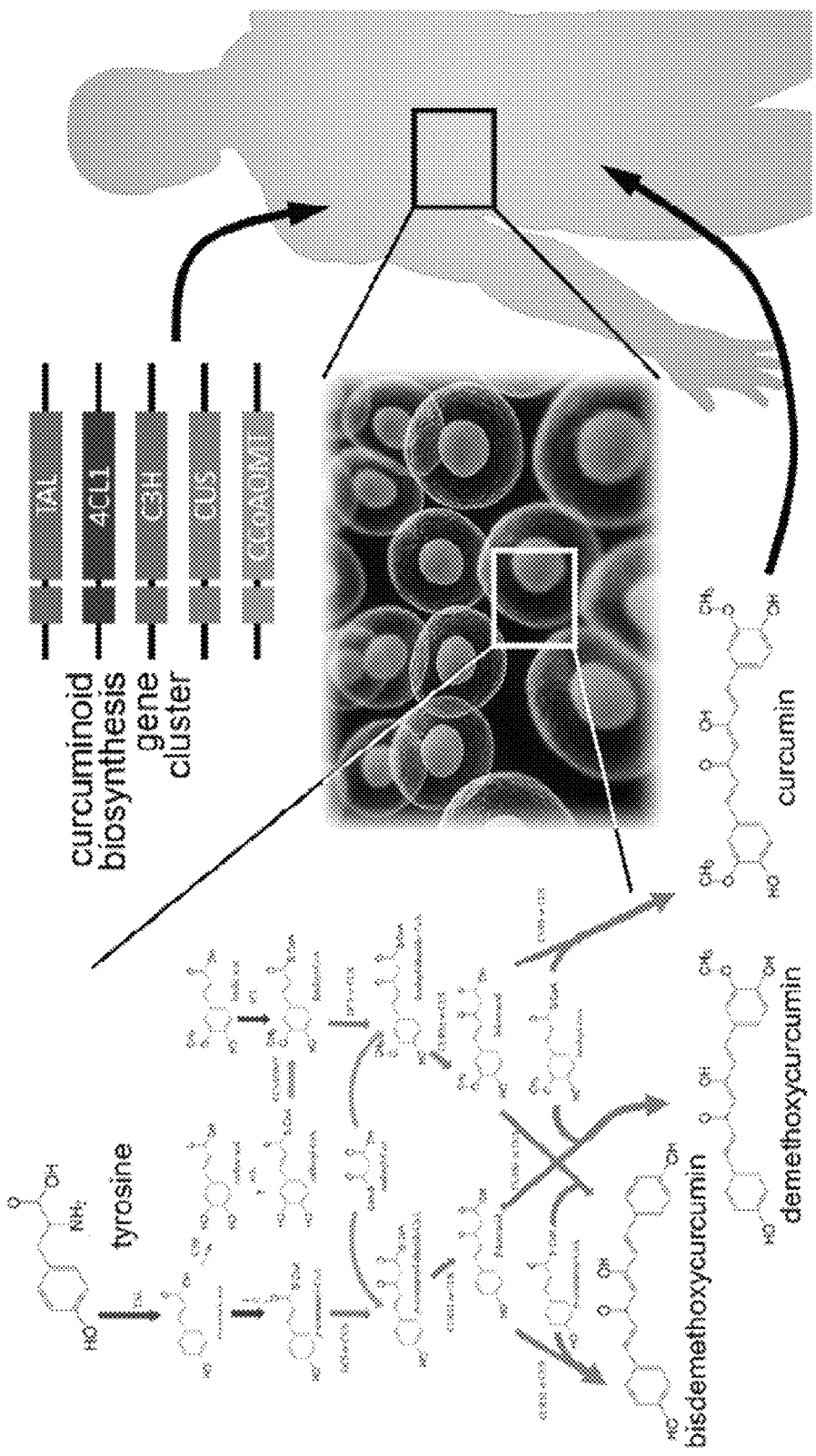
FIG. 3 shows a schematic illustrating in vivo curcuminoid biosynthesis therapy. A cluster of genes encoding enzymes of the curcuminoid biosynthesis pathway are introduced resulting in the patient's own cells producing curcuminoids, which may exhibit therapeutic effects locally or systemically.

More specifically, these Examples demonstrate biosynthesis of curcuminoids by the transient transfection of plasmid cocktails encoding the necessary plant-derived enzymes into HEK293 cells (FIG. 3). In particular, the following Examples identify rate-limiting steps in the enzymatic pathway and describe curcuminoid biosynthesis by engineering relative enzyme expression levels and generating human codon-optimized genes to ensure strong enzyme expression. Also discussed herein is generating cell lines stably expressing the enzymes at optimal levels and, ultimately, under the control of an antioxidant response element. Furthermore, these Examples investigate the potential of this approach in vivo by (i) adeno-associated viral serotype 8 (AAV8) transfection to generate curcuminoid-producing cells in the liver of mice, and (ii) investigating efficacy of in-vivo curcuminoid biosynthesis in an established Syrian hamster model of oral mucositis. The heterologous production of curcuminoids discussed herein serves as the proof-of-principle for a paradigm-shifting therapeutic approach based on in-vivo drug biosynthesis.

Example 1—Demonstrate Enzyme Expression Levels and Curcuminoid Production

Curcuminoids comprise two phenylpropanoid units derived from phenylalanine connected by a central linker derived from malonyl-CoA and are produced in plants by type III polyketide synthases. Each of the genes encoding for these enzymes in the *C. longa* pathway have been functionally characterized, providing detailed biochemical assessments for each of the enzymes. Thus, introduction of a gene cluster encoding the required enzymes into an organism will result in biosynthesis of curcuminoids from an amino acid—phenylalanine and tyrosine—and malonyl-CoA as starting materials. The most successful strategy to date has been combinatorial biosynthesis, which consists of engineering novel gene clusters encoding enzymes from different species, for heterologous production of curcuminoids in *E. coli*. A variety of systems have been reported, using different combinations of enzymes, to produce curcuminoids and similar phytochemicals in a range of microorganisms. However, curcuminoids have not yet been produced in yeast or any eukaryote.

Figure 4:
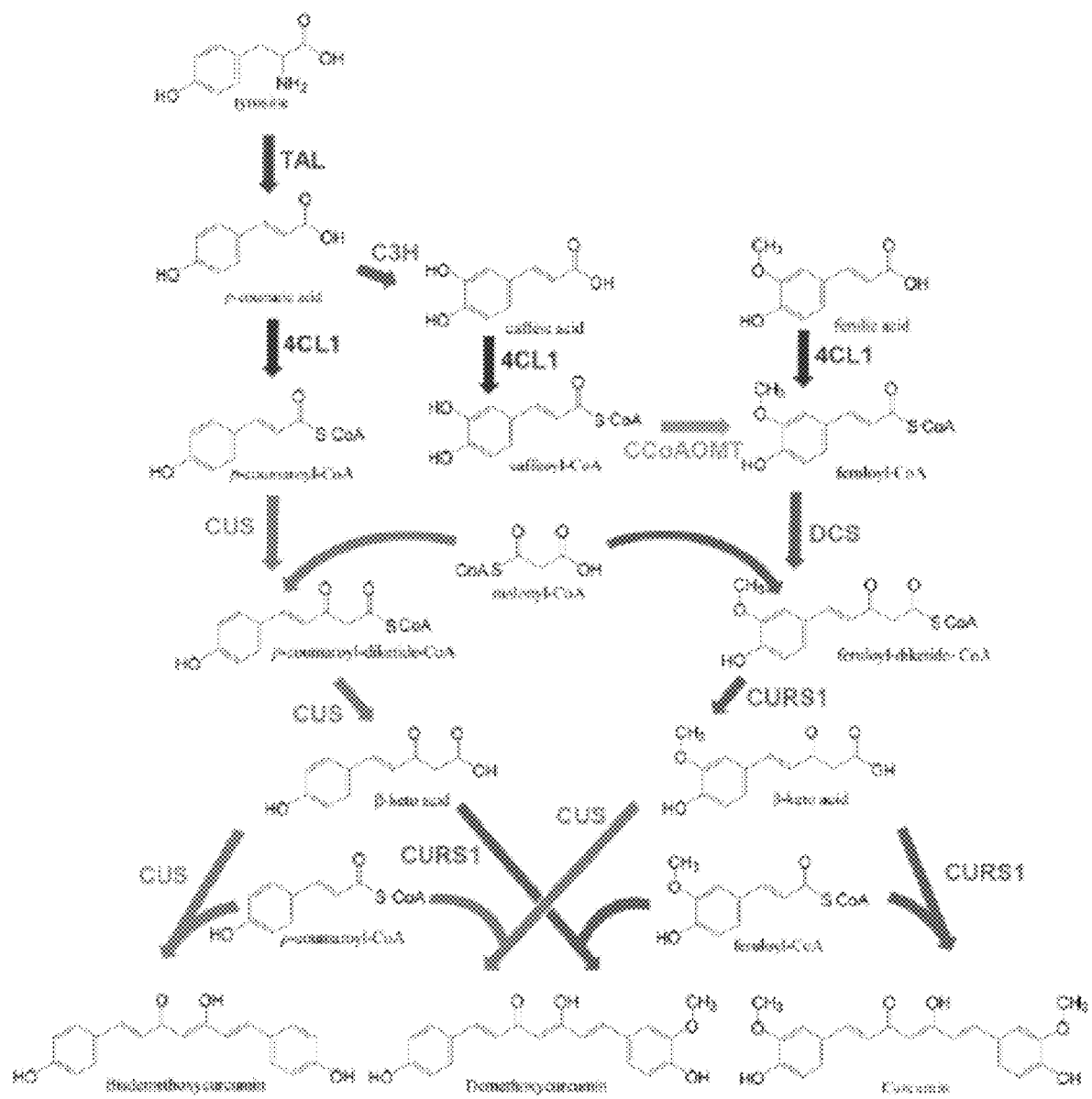
FIG. 4 shows a schematic illustrating an overview of the curcuminoid biosynthesis pathway.

Curcuminoids comprise a complex family of compounds that can be generated from several precursor molecules. This Example employs a gene cluster that produces CCM, dCCM, and ddCCM from tyrosine in ~1 mg/mL quantities in *E. coli* (FIG. 4). Briefly, tyrosine ammonia lyase (TAL, from *Rhodotorula glutinis*) converts tyrosine to p-coumaric acid. A 4-coumarate-CoA ligase (4CL1, from *Arabidopsis thaliana*) adds a coenzyme A unit to form p-coumaroyl-CoA, which is converted to ddCCM in a multi-step reaction catalyzed by curcuminoid synthase (CUS, from *Oryza sativa*). In addition, 4CL1/CUS can convert ferulic acid—if present in sufficient quantities—to CCM and dCCM. Finally, inclusion in the gene cluster of 4-coumarate-3-hydroxylase (C3H, from Saccharothrix espanaensis) converts p-coumaric acid to cinnamic acid, and after addition of a CoA unit by 4CL1, caffeoyl-CoA is converted to feruloyl-CoA by caffeoyl-CoA O-methyltransferase (CCoAOMT, from *Medicago sativa*) providing synthesis of CCM and dCCM from tyrosine rather than ferulic acid. Alternatively, a diketide-CoA synthase (DCS) and curcumin synthase (CURS1) may be used instead of CUS to provide CCM and/or dCCM. In summary, TAL/4CL1/CUS can convert tyrosine to ddCCM, 4CL1/CUS can convert ferulic acid to CCM and dCCM, and TAL/C3H/4CL1/CCoAOMT/DCS/CURS1 (or CUS in place of DCS/CURS1) can convert tyrosine to all three curcuminoids.

To demonstrate the feasibility of biosynthesis of curcuminoids by human cells, each of the genes in the curcuminoid biosynthesis cluster (TAL, 4CL1, CUS, C3H, CCoAOMT, CURS1, and DCS) were synthesized and inserted into a pcDNA3.1 mammalian expression vector under control of the CMV enhancerpromoter, which provides high-level expression. Cells were transfected (using a highly efficient polyethylenimine (PEI) derivative developed in the PI's lab) with a mixture of plasmids encoding cocktails of enzymes in the curcuminoid pathway described above (FIG. 4). For example, HEK293 cells were transfected with a 1:1 (w:w) mixture of plasmids encoding 4CL1 and CUS, and the cell media was supplemented with 0.30 mM p-coumaric acid. After 48 h, the cell media exhibited a deep yellow color, suggesting the presence of ddCCM (FIG. 5A). In another experiment, HEK293 cells were transfected with the 4CL1/CUS cocktail, and the media was supplemented with 0.05 mM ferulic acid. In this case, after 48 h, the media appeared orange, suggesting the presence of CCM. In addition to the production of ddCCM from p-coumaric acid by co-transfection with 4CL1/CUS and the production of CCM from ferulic acid by co-transfection with 4CL1/CUS discussed above, ddCCM was produced from tyrosine by TAL/4CL1/CUS, dCCM was produced from p-coumaric acid by 4CL1/C3H/CCoAOMT/CUS, and CCM was produced from ferulic acid by 4CL1/DCS/CURS1. Subsequently, cell media extracts were prepared in ethyl acetate, concentrated (FIG. 5B), and analyzed for curcuminoids by HPLC compared to authentic standards of ddCCM, dCCM, and CCM (FIGS. 5C-D). Quantitation of the HPLC traces indicated that the curcuminoids were uniquely present in the cell media at concentrations of 10-100 nM. Similar production levels of curcuminoids were achieved in MDA-MB-231 breast cancer cells and MC3T3 murine fibroblasts.

Figure 6A:
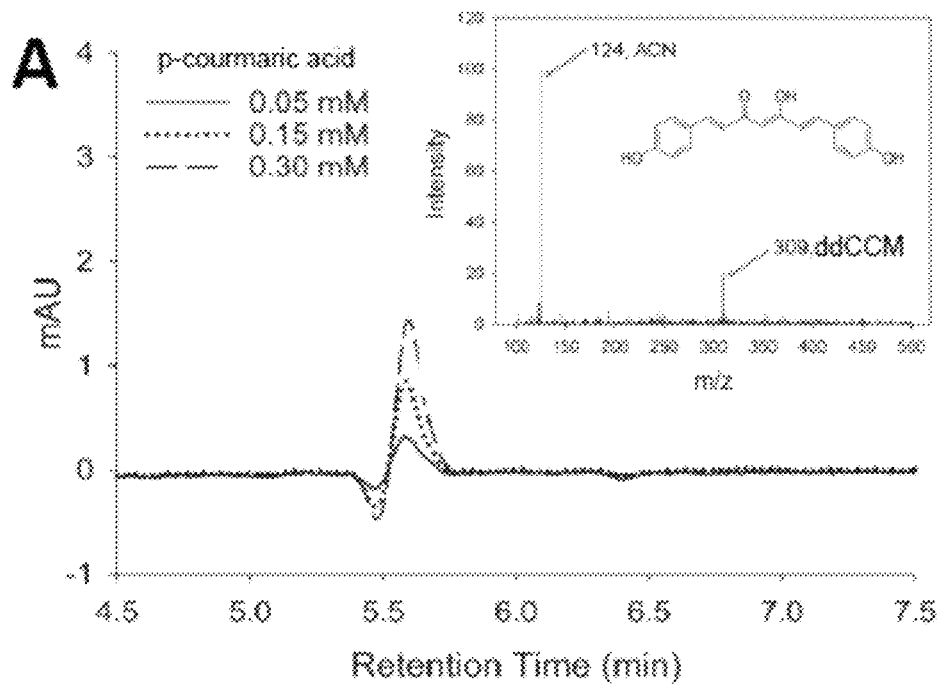
FIGS. 6A-B show graphs illustrating (A) p-coumaric acid and (B) ferulic acid, and the corresponding MS spectra verifying the molecular weight of ddCCM and CCM. (A) Cells were transfected with 4CL1/CUS and cell media were supplemented with the indicated concentrations of p-coumaric acid for 48 h. (B) Cells were transfected with 4CL1/DCS/CURS1 and cell media were supplemented with the indicated concentrations of ferulic acid for 48 h. Curcuminoids were extracted from the media and subjected to HPLC and LC/MS analysis.
Figure 6B:
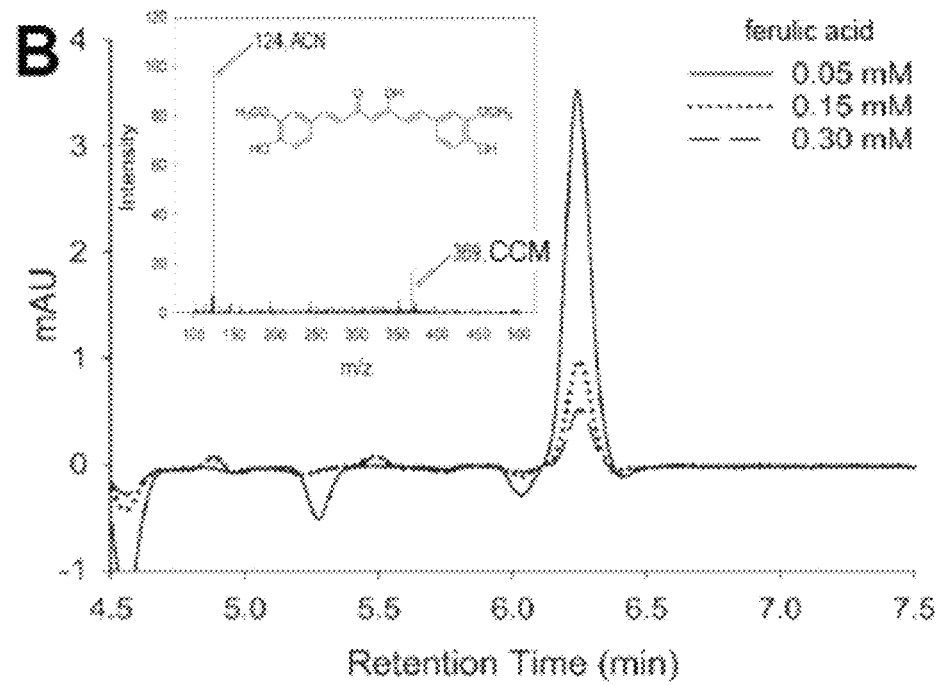

To verify that the curcuminoids were being produced from the starting materials supplemented in the media, the effect of varying the concentrations of starting materials on the curcuminoid production (FIGS. 6A-B) was investigated. As expected, ddCCM production increased with p-coumaric acid concentration. Surprisingly, however, CCM levels decreased with ferulic acid concentration, possibly to do cytotoxicity of ferulic acid at higher concentrations. In addition, mass spectrometry verified that the molecular weight of the products was identical to the expected curcuminoids (FIG. 6A-B, inset).

Investigation of Rate-Limiting Steps in the Curcuminoid Biosynthesis Pathway.

Initially, cells were transfected with appropriate plasmid cocktails (4CL1/CUS, TAL/4CL1/CUS, 4CL1/DCS/CURS1, or 4CL1/C3H/CCoAOMT/CUS) in equal amounts of each plasmid, resulting in biosynthesis of the targeted curcuminoids. However, it was subsequently found that varying the ratio of the plasmids could lead to higher curcuminoid production (Table 1), indicating that modifying the relative enzyme expression levels affects the resulting curcuminoid production.

TABLE 1

Optimal enzyme delivery ratio and supplementation conditions for the production of bisdemethoxycurcumin (ddCCM), demethoxycurcumin (dCCM), and curcumin (CCM).

| | | | Conditions | | | |
|---|---|---|---|---|---|---|
| | | Plasmids | Delivery Ratio | Substrate | [Substrate] | Product |
| Curcuminoid | ddCCM | TAL, 4CL1, CUS | 0.5:1:1 | tyrosine | 0.6 mM | 0.03 uM |
| | ddCCM | 4CL1, CUS | 1:1 | p-coumaric acid | 0.30 mM | 0.05 uM |
| | dCCM | 4CL1, C3H, CCoAOMT, CUS | 1:2:0.5:1 | p-coumaric acid | 0.30 mM | 0.01 uM |
| | CCM | 4CL1, DCS, CURS1 | 1:1:1 | ferulic acid | 0.05 mM | 0.16 uM |

Addition of Acetyl-CoA Carboxylase to Increase Malonyl-CoA Pool.

Malonyl-CoA plays an important role in chain elongation during fatty acid synthesis and, as in the present system, in polyketide synthesis by various organisms. The biosynthesis pathway utilized in most reports of heterologous curcuminoid production relies on the native cellular malonyl-CoA pool to produce the diketides p-coumaroyl-diketide-CoA and feruloyl-diketide-CoA (FIG. 4). In view thereof, the effects on the malonyl-CoA pool of supplying increased malonic acid and/or disodium malonate in the growth media, or of adding an ACC-encoding plasmid to the transfection cocktails, were evaluated.

Example 2—Engineer Cell Lines Producing Curcuminoids Stably and Under Control of an Antioxidant Response Element Due to the anticancer, antioxidant, and anti-inflammatory properties exhibited by curcuminoids, (i) a curcuminoid-producing gene cluster may be introduced to host cells in vivo (FIG. 3) or (ii) host cells may be removed, transfected with a curcuminoidproducing gene cluster ex vivo, and re-implanted in their native site or as encapsulated "cellular curcuminoid factories" to provide gene/cellular therapies. Such therapies utilize a system providing either stable, constitutive biosynthesis of curcuminoids or induction of curcuminoid biosynthesis in response to biological or exogenous stimuli. This Example describes the feasibility of this approach through generation of stable curcuminoid-producing clones and production of curcuminoids in response to oxidative stress by placing the curcuminoid biosynthesis pathway under control of an antioxidant response element (ARE).

Generate Stable Curcuminoid-Producing Cell Lines.

Figures 7A, 7B:
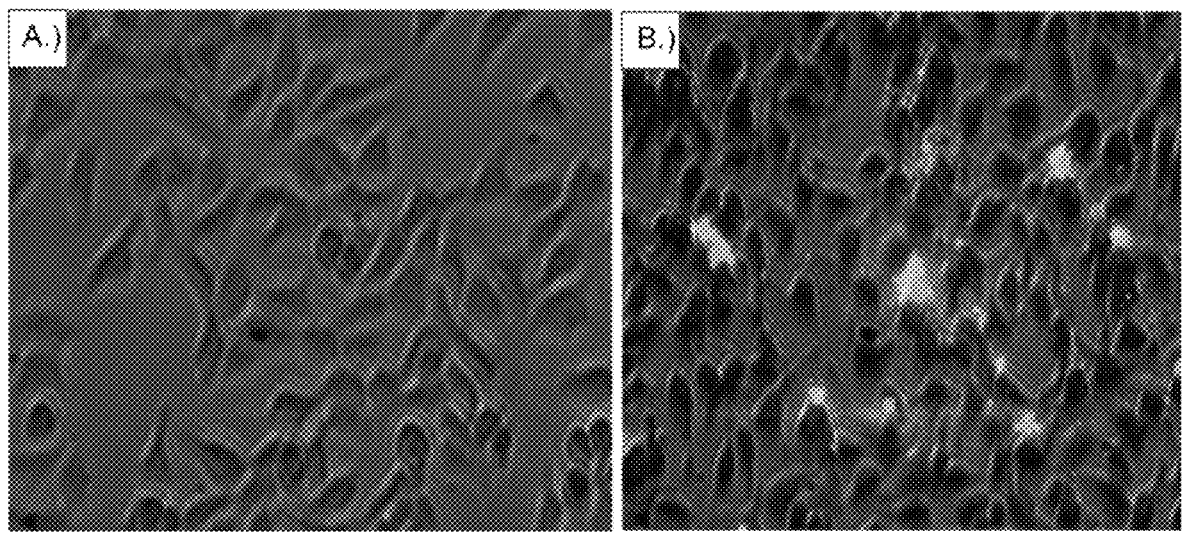
FIGS. 7A-B show fluorescent images comparing (A) control cells and (B) curcumin-producing cells. HEK293 cells were transfected with a pGL3 luciferin reporter gene and a CCM plasmid cocktail and allowed to grow under 0.05 mM ferulic acid supplementation for 48 h. After two days, growth media was aspirated, and cells were washed twice with PBS before imaging. A composite 20× brightfield and FITC image was constructed using a Zeiss ApoTome inverted confocal microscope.
Figure 8:
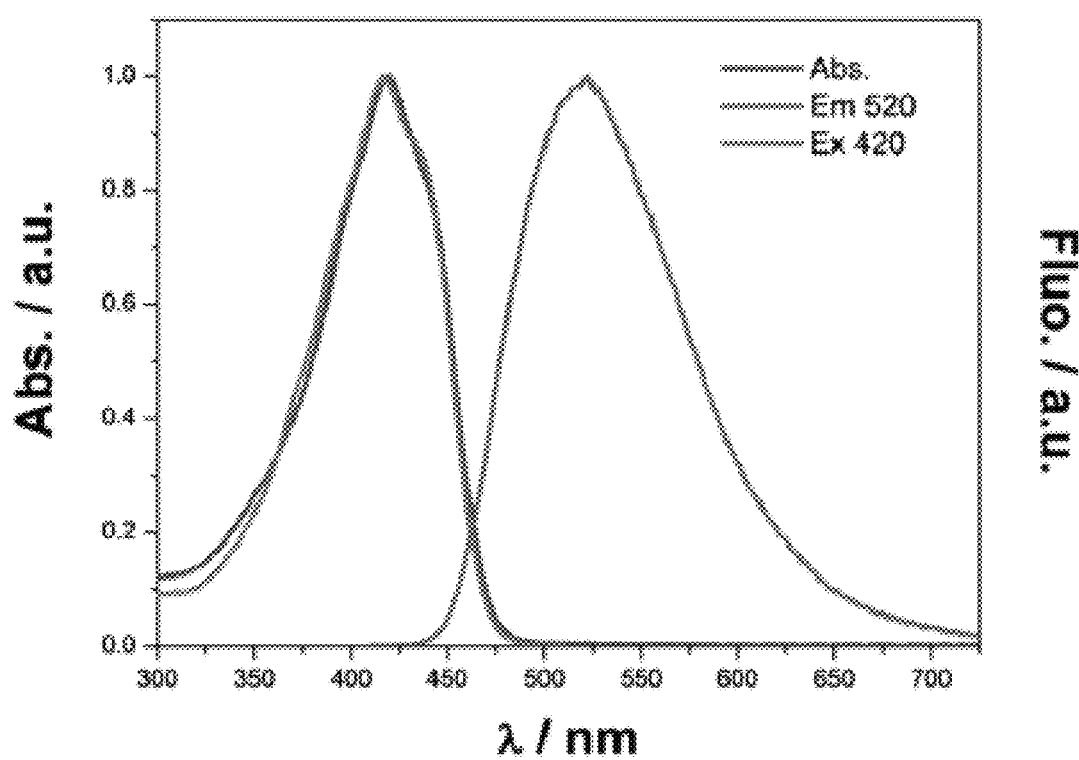
FIG. 8 shows a graph illustrating absorbance, excitation, and emission spectra of CCM in aqueous solution.

HEK293 cells may be engineered to stably express the curcuminoid biosynthesis pathway(s) using CRISPR/Cas9 technology to integrate the genes into the host genome at a selected non-coding locus. The curcuminoids are fluorescent, with excitation and emission wavelengths that can be observed in the FITC channel of common microscopes and cytometers (FIGS. 7A-8). Thus, curcuminoid production can be verified by fluorescence microscopy and separate curcumin-producing cells from non-producing cells can be verified by fluorescence-assisted cell sorting (FACS).

CRISPR/Cas9 allow simultaneously insertion of up to six or more genes at a single locus from a single donor strand (e.g., synthesizing donor strand sequences incorporating appropriate promoters and bicistronic elements). For example, CRISPR/Cas9 provides simultaneous insertion of TAL, 4CL1, and CUS in a single locus to generate a cell line capable of producing ddCCM from tyrosine (HEK293-ddCCM). The generation of HEK293-CCM cells capable of producing CCM from tyrosine includes insertion of 5-6 genes: TAL, 4CL1, C3H, CCoAOMT, and DCS/CURS1 (or CUS). This may include inserting all of the genes from a single donor strand, or building the CCM pathway in a step-wise fashion.

In the step-wise method, for example, the 4CL1 and DCS/CURS1 genes are inserted initially, the media is supplemented with ferulic acid, and the fluorescent CCM-producing cells are isolated. Subsequently, CCoAOMT and C3H are inserted and CCM-producing cells are isolated in media supplemented with pcoumaric acid. Finally, TAL is inserted to generate HEK-CCM cells capable of biosynthesis of CCM from tyrosine. To provide some enzymes in higher quantities than others, multiple copies of those genes may be inserted. The metabolomic profiles of the final cell lines (and intermediates) may be compared to native HEK293 cells to ensure no adverse effects on primary metabolism.

As an alternative to CRISPR/Cas9 technology in the construction of stable cell lines, lentiviral vectors may be used. Like CRISPR/Cas9, lentiviruses are capable of integrating recombinant genes in the host genome. However, the size of recombinant sequences that can be packaged by lentiviruses is limited, and thus may involve more transfection steps to build the entire curcuminoid biosynthesis pathway. In addition, the locus of lentiviral vector-mediated insertions cannot be controlled.

Generate Stable Cell Lines Producing Curcuminoids Under Control of an Antioxidant Response Element.

Oxidative stress—elevated levels of reactive oxygen species (ROS), reactive nitrogen species (RNS), and electrophilic species, or reduced antioxidant (i.e., glutathione) capacity—plays a role in a number of disease states including inflammatory disease, certain cardiovascular diseases, hypoxia, neurodegenerative disease, and metabolic disorders. An important element of the cellular response to oxidative stress is activation of the Nrf2-ARE pathway. Oxidative stress leads to an increase in nuclear factor E2-related factor 2 (Nrf2) levels in the nucleus; whether this response is due to increased Nrf2 expression or reduction of proteasomal Nrf2 degradation is debated. Nrf2 interacts with a cis-acting enhancer ARE (TGAG/CNNNGC) found in the promoters of two major detoxification enzymes, glutathione S-transferase A2 (GSTA2) and NADPH:quinone oxidoreductase 1 (NQO1), initiating their expression.

Figures 9, 10:
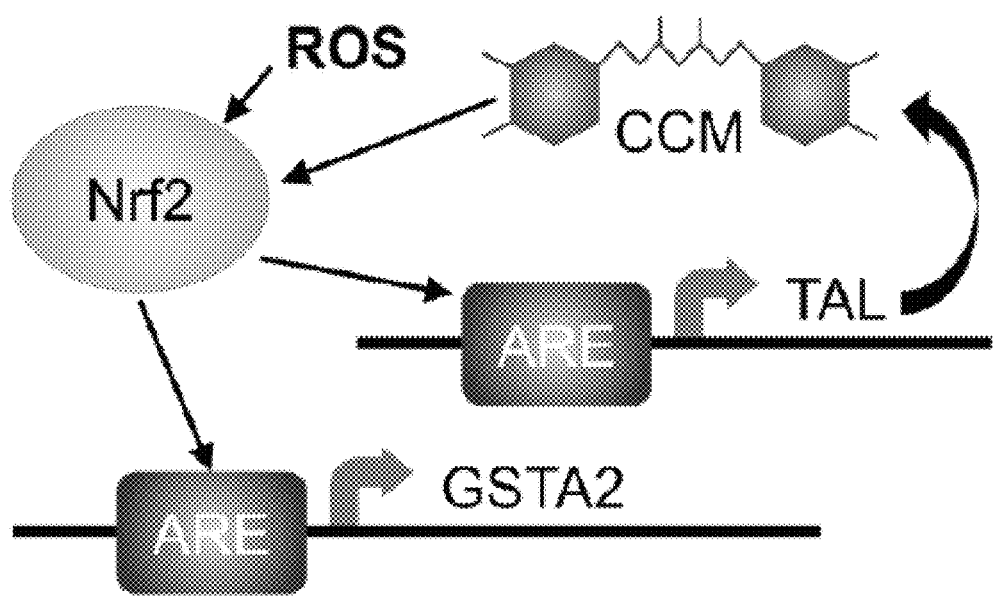
FIG. 9 shows a schematic illustrating ARE-controlled curcuminoid production and feedback loop. The presence of reactive oxygen species (ROS) upregulates transcription of Nrf2, which binds the ARE and activates expression of cytoprotective enzymes such as GSTA2. In the present construct, ARE activation also initiates expression of TAL, leading to biosynthesis of curcuminoids (CCM). CCM is known to upregulate expression of Nrf2, providing amplification of CCM biosynthesis and transcription of cytoprotective enzymes.
FIG. 10 shows an image illustrating example alignment of the first 20 codons from R. glutinis TAL (wtTAL) (SEQ ID NO: 1), human codon optimized sequence predicted by GeneOptimizer (hTAL) (SEQ ID NO: 2), and preferred human codon optimized sequence (pTAL) (SEQ ID NO: 3).

Therefore, to provide synthesis of curcuminoids in response to oxidative stress and generate stable HEK293-ddCCM$_{ARE}$ and HEK293-CCM$_{ARE}$ cell lines, the curcuminoid biosynthetic cluster(s) may be engineered under the control of GSTA2 and NQO1 promoters following the strategy described above. The presence of ROS or reduction of glutathione will increase Nrf2 levels, turning on curcuminoid biosynthesis. Interestingly, it has been demonstrated that CCM increases the expression of Nrf2 and, subsequently, GSTA2. This is believed to provide a positive feedback in which induction of Nrf2 turns on curcuminoid biosynthesis, which in turn increases expression of Nrf2, driving further production of curcuminoids (FIG. 9).

Placing TAL under control of the ARE is believed to provide oxidative stress-induced production of curcuminoids (e.g., ARE-TAL/4CL1/CUS for stimulus-responsive production of ddCCM). However, additional enzymes (e.g., 4CL1 and CUS) may be placed under control of the ARE to provide a more robust and non-leaky stimulus-responsive curcuminoid biosynthesis. Furthermore, the ARE elements may be amended with attenuation or enhancer elements to provide additional coarse control elements. To investigate oxidative stress-induced curcuminoid biosynthesis, HEK293-ddCCM$_{ARE}$ and HEK293-CCM$_{ARE}$ may be cultured in normal growth media and in the presence of H$_2$O$_2$, followed by comparison of TAL mRNA and expression and curcuminoid production.

Human Codon Optimization.

The frequency of codon usage varies greatly among organisms, and protein expression resulting from two mRNAs encoding the same polypeptide but using synonymous codons can vary dramatically. As a result, codon optimization of heterologous genes has been used to maximize protein expression in host cells including bacteria, yeast, plants, and mammals. Many codon-optimization approaches have been reported, and codon-optimization programs and commercial services are available. Although the various approaches differ primarily in how codon bias is measured, they generally avoid using rare codons, which are thought to decrease the rate of translation. Further, the various approaches use the most frequently used codon for all instances of an amino acid, adjust codon usage so that it is proportional to the natural distribution of the host organism, use codons that are thought to correspond to abundant tRNAs, and/or avoid occurrences of codon pairs that are known to translate slowly.

As an example, Inouye et al. compared expression of six bioluminescence-catalyzing enzymes—aequorin, clytin II, *Gaussia princeps* luciferase (Luc), *Renilla reniformis* Luc, *Photinus pyralis* Luc, and *Luciola cruciate* Luc—using the wild-type genes and codon-optimized genes in which each codon was replaced with the synonymous codon most common in human genes ("preferred codon" optimization). In HEK293, HepG2, COS-1, HeLa, and Gin-1 cell lines, the preferred-codon genes produced 10- to 20-fold higher protein levels compared to the wild-type genes. In another example, tamavidin 2, an avidin analog from the mushroom *Pleurotus cornucopias*, was produced at 30-fold higher concentrations using a preferred-codon gene and 20-fold higher using a commercially codon-optimized sequence compared to the wild-type gene in HEK293 cells. Without wishing to be bound by theory, it is believed that codon usage may limit translation of the plant-derived genes in the curcuminoid biosynthesis pathway. Accordingly, codon optimization of these genes may increase expression of the enzymes and, ultimately, curcuminoid production.

On the other hand, there is evidence to suggest that the presence of specific codons in natural mRNAs have evolved in response to diverse selective pressures at both the RNA and protein levels. As a result, synonymous codon changes can have unexpected consequences and may affect protein conformation and stability, change sites of post-translational modifications, or alter protein function. Furthermore, synonymous-codon mutations have been linked to disease. A reason for these unanticipated effects is that codon usage is thought to control the rate of nascent protein elongation, causing ribosomes to slow down or pause at certain sites, which may be necessary in some cases for correct protein folding. For example, Hu et al. investigated 342 antibody constructs with synonymous codon variants and identified altered solubility and epitope binding affinities of the resulting antibodies. Similarly, synonymous codon changes in a fluorescent-protein gene led to altered protein folding, resulting in different fluorescent properties.

To determine if codon optimization can enhance enzyme expression and curcuminoid production, 4CL1 and CUS genes are synthesized with codon usage chosen by several different approaches: preferred-codon optimization, GeneOptimizer™ (GeneArt GmbH), Integrated DNA Technologies codon optimization tool (www.idtdna.com/CodonOpt), and GenScript's proprietary optimization service (www-.genscript.com/codon-opt.html) (FIG. 10). The resulting genes are used to transfect HEK293 cells, and ddCCM production, the percent of ddCCM-producing cells, enzyme expression (Western blots), and enzyme mRNA levels (quantitative reverse-transcriptase PCR, qRT-PCR) are quantified from p-coumaric acid.

Example 3—Investigate Efficacy of Curcuminoid-Producing Cells In Vitro and In Vivo In Vitro Assays of Curcuminoid Antioxidant Activity.

Oxidative stress occurs when the balance of oxidants and antioxidants is perturbed, leading to the excess production of ROS and RNS. High levels of ROS and RNS lead to cellular damage by lipid peroxidation, protein carbonylation, and DNA damage. In the presence of oxidative stress, mitochondria are key organelles for ROS production and are sensitive targets of ROS- and RNS-induced damage. Mitochondria are affected by lipid peroxidation, leading to generation of hydrogen peroxide and superoxide radicals, thus resulting in additional ROS production, mitochondrial dysfunction (disturbing the normal respiration mechanism and loss in ATP production), and ultimately cell necrosis and apoptosis. As a result, mitochondrial oxidative stress becomes the indirect cause of many diseases, including inflammatory disease, cancers, neurological disorders, and cardiovascular disease. The ability of curcuminoids to scavenge free radicals provides protection from these damaging effects.

This Example is directed to investigating and quantifying the bioactivity of biosynthesized curcuminoids in cells in vitro and, ultimately, in in vivo disease models. A set of standard antioxidant activity assays is employed to quantify curcuminoid bioactivity, including enhancing the mitochondrial respiratory capacity and redox metabolism, and the effects of intracellular curcuminoids on expression and activity of important cytoprotective enzymes in the transient and stable curcuminoid-producing cell lines in vitro. In addition, pharmacokinetics, biodistribution, and toxicology of curcuminoids produced following AAV-mediated transfection of murine liver, and a hamster model of oral mucositis for evaluating the efficacy of heterologous curcuminoid biosynthesis in vivo, are investigated.

Curcuminoids exhibit potent antioxidant activity due to the ability of the phenol and ketone moieties to scavenge free radicals. Thus, a battery of assays is used to investigate the efficacy of biosynthesized curcuminoids to protect the curcuminoid-producing cells against oxidative stress. (i) The antioxidant activity of curcuminoids is quantified in conditioned media from and lysates of curcuminoid-producing cells using the Trolox equivalent antioxidant capacity assay. This assay relies on the scavenging of 2,2'-azinobis(3-ethylbenzothiazoline-6-sulfonic acid) radical anions (ABTS$^{.-}$), which absorb at 734 nm, to generate reduced ABTS$^{2-}$, which is colorless. ABTS$^{.-}$ is mixed with conditioned media and lysates, the absorbance is measured after 5 min, and compare to the antioxidant activity of known concentrations of Trolox to determine the "mM Trolox equivalence." (ii) The cytotoxicity of intracellular curcuminoid biosynthesis is investigated using an ApoTox-Glo assay (Promega), which provides data on cellular metabolism, cell death, and induction of apoptosis. The same assay is also used to determine the ability of curcuminoids to protect cells from challenge with increasing concentrations of $H_2O_2$. (iii) ROS in curcuminoid-producing cells in the presence of $H_2O_2$ is quantified using a fluorescent DCF assay (87). 2',7'-Dichlorodihydrofluorescein diacetate (DCF-DA) is a nonfluorescent, cell-permeable dye that is hydrolyzed by cellular esterases to its polar DCFH form, which is retained in cells. DCFH can be oxidized by intracellular ROS to form the fluorescent species 2',7'-dichlorofluorescein (DCF). Thus, upon treatment of cells with DCF-DA and $H_2O_2$, DCF fluorescence is a measure of intracellular ROS levels, and the decrease in fluorescence relative to non-treated (noncurcuminoid-producing) controls indicates antioxidant activity. (iv) The effects of $H_2O_2$ challenge on mRNA (qRT-PCR), and expression (Western blots) of cytoprotective enzymes Nrf2, GST, and heme oxygenase-1, which are known to be upregulated in response to ROS, are also quantified.

Figure 11:
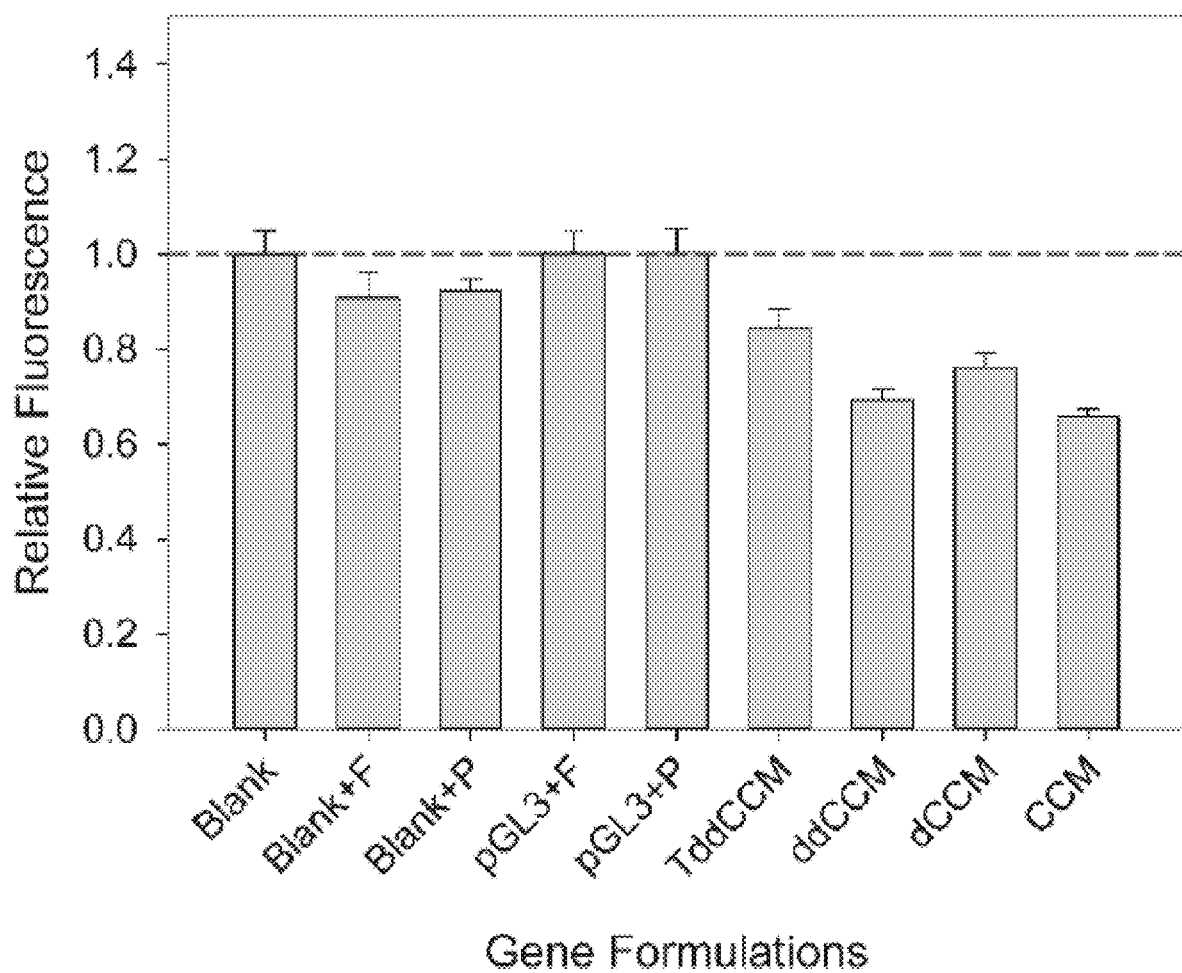
FIG. 11 shows a graph illustrating relative radical scavenging ability of cells producing curcuminoids. Cells were exposed to 1 mM $H_2O_2$ for 30 min before incubation with CellROX Deep Red. Blank: untransfected cells. F: ferulic acid-supplemented media. P: p-courmaric acid-supplemented media. pGL3: luciferase-encoding plasmid.

Additionally, the antioxidant potential of heterologously produced curcuminoids was investigated using CellROX Deep Red (Invitrogen, Carlsbad, Calif.), a fluorogenic probe for cellular oxidative stress. The cell-permeable CellROX dye is non-fluorescent in its reduced state but becomes highly fluorescent upon oxidation by reactive oxygen species (ROS) within cells. Cells were treated with 1 mM $H_2O_2$ to induce oxidative stress and subsequently incubated with CellROX before quantifying the resulting fluorescence (FIG. 11). Neither the presence of p-coumaric acid nor ferulic acid, nor transfection with pGL3 (encoding luciferase), had any effect on CellROX oxidation. However, cells transfected with TAL/4CL1/CUS in the presence of tyrosine (TddCCM), 4CL1/CUS in the presence of p-coumaric acid, 4CL1/C3H/CCoAOMT/CUS in the presence of p-coumaric acid, and 4CL1/DCS/CURS1 in the presence of ferulic acid resulted in reduced CellROX fluorescence, indicating protection from $H_2O_2$-induced oxidative stress. The largest effect, 37% reduction in CellROX fluorescence, was observed in cells producing CCM from ferulic acid, which also exhibited the highest concentration in cell media (Table 1). It is important to note that this statistically significant antioxidant effect was observed with only a small fraction of cells producing the curcuminoids, and a much greater effect is expected under different delivery conditions and/or with curcuminoid-producing clones.

Figure 12:
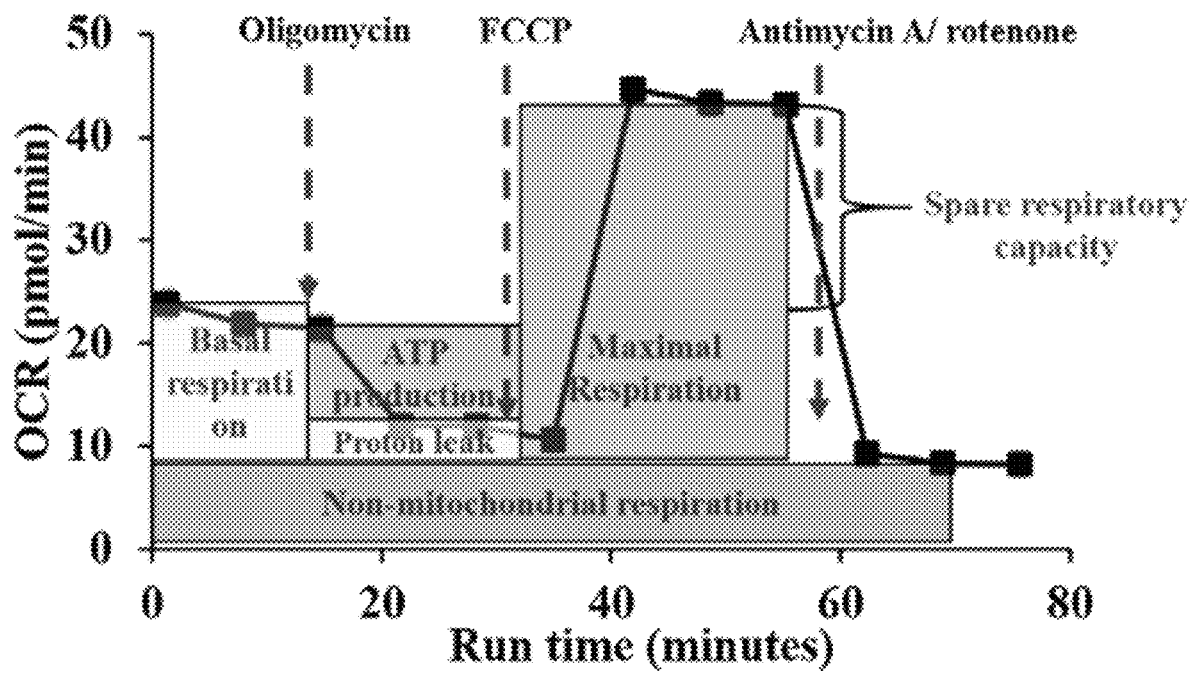
FIG. 12 shows a graph illustrating mitochondrial OCR profile of a typical mitochondrial stress assay conducted by the Seahorse XF instrument.

The cytoprotective effect of intracellularly biosynthesized curcuminoids is investigated using a mitochondrial stress assay (Seahorse XF analyzer) that monitors real-time mitochondrial bioenergetics and cellular metabolic profile. In short, the mitochondrial stress assay measures oxygen consumption and extracellular acidification rates upon sequential injections of inhibitors: oligomycin A, which acts as an ATP synthase inhibitor; FCCP, an uncoupling agent; and a mixture of rotenone and antimycin A, which are inhibitors of mitochondrial respiratory chain complex I and III and shut down mitochondrial oxygen consumption (FIG. 12). Oxidative stress caused by addition of $H_2O_2$ leads to decreases in basal respiration, ATP production, and maximal respiration. Intracellular curcuminoids are believed to limit or eliminate the effects of oxidative stress on mitochondrial function upon challenge with increasing concentrations of $H_2O_2$.

Investigate the Effects of Curcuminoid Biosynthesis on Proliferation and Migration of Breast Cancer Cells In Vitro.

Curcumin has been shown to exhibit anti-proliferative effects in a variety of cancer cell lines including prostate, lung, colon, and breast cancers. In addition, curcumin was found to downregulate multidrug resistance proteins and P-glycoprotein and have the potential to overcome multidrug resistance. Although the exact mechanism of these effects is not clear, curcumin has been shown to inhibit NF-kB, AP-1, STAT3, etc., as described above. It has also been reported that curcumin inhibits fatty acid synthase (FAS) and induces apoptosis by upregulating Bax (a pro-apoptotic protein that plays a key role in mitochondrial stress-induced cell apoptosis) and down-regulating the anti-apoptotic protein Bcl-2. As such, the effects of intracellular curcuminoid biosynthesis on proliferation, migration, and apoptosis of human cancer cell lines including MDA-MB-231, breast cancer; HeLa, cervical cancer; and U-87 MG glioblastoma cells is investigated. The cells are transfected with a curcuminoid biosynthesis gene cluster (e.g., TAL/4CL1/CUS)—transiently or, preferably, stably via CRISPR/Cas9—as described above. After confirming curcuminoid production levels, the effects of curcuminoids on proliferation and apoptosis (ApoTox-Glo assay), and migration using 2D scratch and Boyden chamber assays, is quantified. In addition, the effects of curcuminoid biosynthesis on expression (Western blots) and mRNA levels (qRT-PCR) of FAS, Bax and Bcl-2 is quantified.

Demonstration of In Vivo Curcuminoid Biosynthesis.

In some cases, such as the antioxidant, anti-inflammatory, and anti-cancer applications of curcuminoids, it may be desirable to provide long-term, systemic presence of the drug. As such, a system for production of curcuminoids in the liver of BALB/c mice is developed. The liver was chosen for its relatively large blood flow and ease of transfection. This system includes generating AAV8 vectors, which show tropism for the liver upon i.v. injection, and carrying the genes encoding each of the enzymes in the curcuminoid biosynthesis pathway. AAV does not integrate with the host genome, but expression of AAV-delivered genes is relatively long-lasting (at least 60 days in murine liver). Although the capacity of AAV vectors for packaging recombinant genes is 4.0-4.5 kb, the curcuminoid-producing enzymes are relatively small, ranging in size from 744 bp (CCoAOMT) to 2082 bp (TAL) and, along with their promoters, can be easily packaged by an AAV vector. In addition, AAVs carrying a bicistronic construct that encodes two enzymes that should be expressed at similar levels (e.g., 4CL1/CUS or CURS1/DCS) in the same AAV particle may be designed to simplify the transfection.

Efficacy of In Vivo Curcuminoid Biosynthesis in Prevention of Oral Mucositis.

Oral mucositis (OM) is a common side effect seen in cancer patients receiving chemo- or radiation therapy for head and neck cancers. OM manifests as erythema leading to large, contiguous ulcers that can cover >50% of the oral surface and cause severe pain and hindered oral function. In some cases, severe OM can force the termination of therapy. The current standard of care for OM is primarily palliative, involving intravenous analgesics and hourly analgesic and lubricating oral rinses. The general lack of effectiveness of these treatments along with their high treatment burden result in significant reduction in patient compliance. Oxidative stress, including excessive production of ROS, due to the chemo- and radiation therapy have been clearly linked to development of OM. In particular, oxidation of proteins, lipids, and DNA damages the rapidly replicating oral mucosa. In addition, oxidative stress activates key mediators of pro-inflammatory pathways such as NF-κB, AP-1, and STAT3, leading to the further release of tissue-damaging cytokines and ROS, propagating the cycle of cell death and tissue damage. The apoptotic and necrotic chain of events halts epithelial proliferation, ultimately resulting in ulceration. Because of its antioxidant and anti-inflammatory properties, curcumin was recently shown to reduce the incidence and severity of chemotherapy- and radiation-induced OM in rats and in humans.

Figure 13:
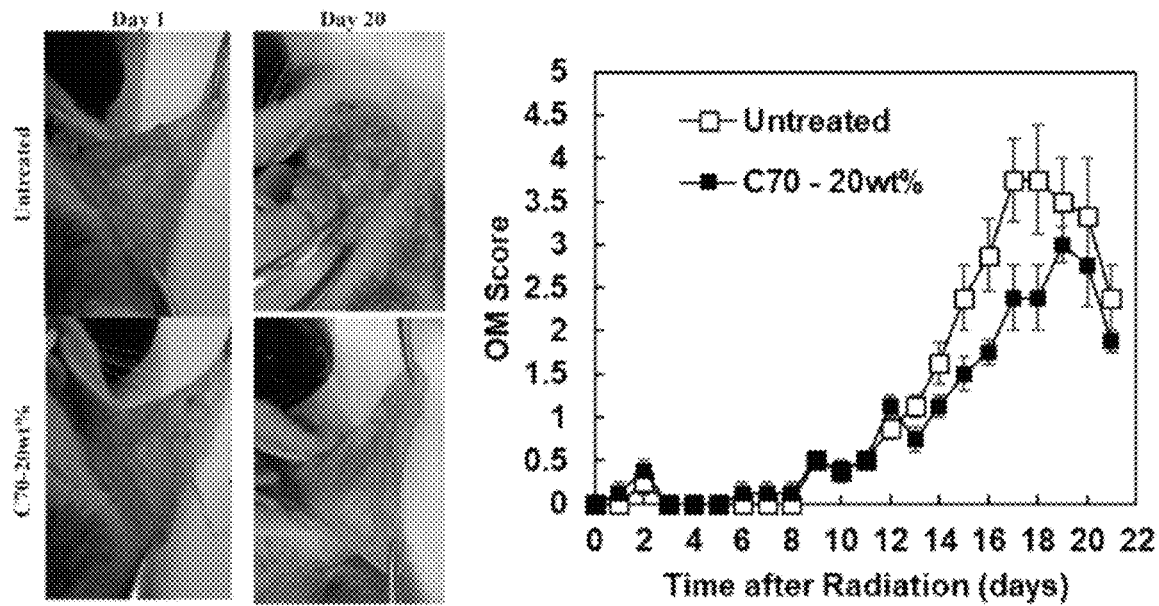
FIG. 13 shows images and a graph illustrating radiation-induced oral mucositis in Syrian hamster cheeks demonstrating the effects of treatment with a curcumin-containing polymer.

The efficacy of in vivo curcumin biosynthesis in prevention of OM is evaluated in a Syrian hamster model of OM, which reliably reproduces key pathophysiological features of OM including the clinical presentation of ulceration and is one of the most frequently used models to investigate OM therapeutics (FIG. 13). Briefly, the hamster is anesthetized, the left cheek pouch is clamped between acrylic sheets to hold it in place, and each cheek pouch is exposed to 60 Gy total irradiation in a linear accelerator (LINAC). The use of the LINAC system provides gamma radiation exposure, is clinically relevant, and provides tight control of the radiation dose, reducing animal-to-animal exposure differences. For up to three weeks after irradiation, the hamsters is weighed daily and cheeks extracted to evaluate injury based on a well-established, validated scale (Table 2).

TABLE 2

Oral mucositis scoring rubric.

| Score | Description |
|---|---|
| 0 | Pouch completely healthy. No erosion or vasodilation. |
| 1 | Erythema, but no evidence of mucosal erosion. |
| 2 | Severe erythema, vasodilation and superficial erosion. |
| 3 | Formation of ulcers in one or more places, but not affecting more than 25% of the surface area of the pouch. Severe erythema and vasodilation. |
| 4 | Cumulative ulcer formation of about 50% of pouch surface area. |
| 5 | Complete ulceration of pouch mucosa. Loss of pliability. |

Equal numbers of male and female hamsters are randomly divided into groups (n=8). Negative controls comprise non-irradiated, non-treated; nonirradiated, treated; and irradiated, nontreated groups. The positive control group comprises animals that are irradiated and subsequently treated with free curcumin in a mucoadhesive solution, containing 5 wt % curcumin at a dose of 50 mg/kg/day beginning two days prior to exposure (the mucoadhesive solution is composed of 3 wt % Noveon, 0.2 wt % Eudragit L100, 0.7 wt % Carbomer 971, 1% glycerin in a 40 mM phosphate buffer solution, adjusted to pH 7.0). The treatment groups are determined based on the curcuminoid production levels, bioavailability, and duration of production achievable in the in vivo systems described above. A preferred treatment is animals stably producing curcuminoids following AAV8-mediated transfection of liver and providing therapeutically relevant curcuminoid concentrations in circulation. The primary alternative is local AAV-mediated transfection of tissues in the cheek pouch. Another alternative approach is HEK293-ddCCM or HEK-CCM cells encapsulated in lysine/alginate spheres and implanted s.c. or i.p. in tissue cages. It is believed that the sustained presence of curcumin significantly reduces severity and duration of OM compared to irradiated hamsters without treatment or with the positive control treatment, which is limited to acute exposure to the free CCM/mucoadhesive solution (comparable to rinses in humans).

Alternative: Efficacy of In Vivo Curcuminoid Biosynthesis on Tumor Growth and Metastasis in a Murine Model of Basal-Like Breast Cancer.

As an alternative to the OM model, the efficacy of in vivo curcuminoid biosynthesis in inhibiting growth and metastasis of orthotopic 4T1 tumors is investigated. Murine 4T1 mammary carcinoma is a widely used model of stage IV human basal-like breast cancer (BLBC). Tumor growth and metastasis of the 4T1 cell line in BALB/c mice very closely mimic human BLBC with spontaneous metastasis primarily to the lungs and brain. Teflon tissue cages containing curcuminoid-producing HEK293-CCM or HEK293-ddCCM cells encapsulated in lysine/alginate beads are subcutaneously implanted. Non-curcuminoid-producing HEK293 cells are similarly implanted as a negative control. The curcuminoid production, pharmacokinetics, biodistribution, and toxicity is evaluated as described above. (If sub-therapeutic levels of curcuminoids are found in circulation, the encapsulated cells may be implanted intraperitoneally.) Subsequently, orthotopic breast cancer tumors are generated by implantation of 4T1-luc cells (stably expressing luciferase) in the abdominal mammary fat pad of female BALB/c mice. Finally, a positive control group receives doxorubicin (Dox). The groups are summarized in Table 3.

TABLE 3

Treatment and control groups for 4T1 orthotopic BLBC model (n = 8)

| Group | Tumor | Treatment |
|---|---|---|
| 1 | No tumor | HEK293-CCM |
| 2 | 4T1 | Sham |
| 3 | 4T1 | HEK293 |
| 4 | 4T1 | HEK293-CCM |
| 5 | 4T1 | Dox, 5 mg/kg Days 0, 4, 8, 12 |

Tumor volume, body weight, and survival are measured for 2 months. Mice are also imaged every 7 days to follow tumor growth and development of metastases. At the time of sacrifice, the primary tumor and major organs are harvested and prepared for histology. Sections are H&E stained to assess necrosis and the invasive behavior of surrounding tissue and to count metastatic nodules. Other sections are immunohistochemically labeled for determination of Ki67 expression (to identify actively proliferating cells), CD31 expression (to identify endothelial cells and determine microvessel density), and apoptosis using the terminal deoxynucleotidyl transferase dUTP nick end labeling (TUNEL) assay. Tumor growth, metastasis, and other endpoints observed for animals with implanted curcuminoid producing cells are compared to those implanted with HEK293 cells (negative control) and Dox-treated animals. To assess the potential of this approach for treatment of existing tumors and metastases, 4T1 tumors are established in the animals prior to implantation of curcuminoid-producing cells.

CONCLUSIONS

As discussed above, a proof-of-principle has been demonstrated by transient transfection of HEK293 cells with cocktails of 2-6 plasmids resulting in biosynthesis of curcuminoids when grown in media supplemented with the appropriate substrates—tyrosine and/or ferulic acid—at ~1 µg/mL in culture media. Additionally, based upon the proof-of-principle, cells stably expressing the biosynthesis gene cluster for constitutive production of curcuminoids may be generated. Furthermore, a curcuminoid biosynthesis gene cluster under the control of an antioxidant response element (ARE) may be created, that will produce curcuminoids in response to oxidative stress. In view thereof, it is believed that (i) engineering of human cells with a gene cluster encoding an appropriate set of enzymes (specific enzymes and combinations to be defined below) provides intracellular biosynthesis of curcuminoids from amino acid starting materials, and (ii) these curcuminoids provide for greater therapeutic activity than conventional, exogenously delivered curcuminoids.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Maheshwari, Radha K., et al. "Multiple biological activities of curcumin: a short review." Life sciences 78.18 (2006): 2081-2087.
2. Naksuriya, O., Okonogi, S., Schiffelers, R. M., & Hennink, W. E. (2014). Curcumin nanoformulations: a review of pharmaceutical properties and preclinical studies and clinical data related to cancer treatment. Biomaterials, 35(10), 3365-3383.
3. Aggarwal, Bharat B., and Kuzhuvelil B. Harikumar. "Potential therapeutic effects of curcumin, the anti-inflammatory agent, against neurodegenerative, cardiovascular, pulmonary, metabolic, autoimmune and neoplastic diseases." *The international journal of biochemistry & cell biology* 41.1 (2009): 40-59.
4. O'Toole, Martin G., et al. "Release-modulated antioxidant activity of a composite curcumin-chitosan polymer." *Biomacromolecules* 17.4 (2016): 1253-1260.
5. Chiu, Tsung-Lang, and Chin-Cheng Su. "Curcumin inhibits proliferation and migration by increasing the Bax to Bcl-2 ratio and decreasing NF-κBp65 expression in breast cancer MDA-MB-231 cells." *International journal of molecular medicine* 23.4 (2009): 469-475.
6. Kunnumakkara, Ajaikumar B., Preetha Anand, and Bharat B. Aggarwal. "Curcumin inhibits proliferation, invasion, angiogenesis and metastasis of different cancers through interaction with multiple cell signaling proteins." *Cancer letters* 269.2 (2008): 199-225.
7. Anand, Preetha, et al. "Bioavailability of curcumin: problems and promises." *Molecular pharmaceutics* 4.6 (2007): 807-818.
8. Prasad, Sandeo, Amit K. Tyagi, and Bharat B. Aggarwal. "Recent developments in delivery, bioavailability, absorption and metabolism of curcumin: the golden pigment from golden spice." *Cancer research and treatment: official journal of Korean Cancer Association* 46.1 (2014): 2.
9. Katsuyama, Y., Matsuzawa, M., Funa, N., & Horinouchi, S. (2007). In vitro synthesis of curcuminoids by type III polyketide synthase from *Oryza sativa*. Journal of Biological Chemistry.
10. Rodrigues, J. L., Araújo, R. G., Prather, K. L., Kluskens, L. D., & Rodrigues, L. R. (2015). Production of curcuminoids from tyrosine by a metabolically engineered *Escherichia coli* using caffeic acid as an intermediate. Biotechnology journal, 10(4), 599-609.
11. Wang, S., Zhang, S., Xiao, A., Rasmussen, M., Skidmore, C., & Zhan, J. (2015). Metabolic engineering of *Escherichia coli* for the biosynthesis of various phenylpropanoid derivatives. Metabolic engineering, 29, 153-159.
12. Fang, Z., Jones, J. A., Zhou, J., & Koffas, M. A. (2018). Engineering *Escherichia coli* Co-Cultures for Production of Curcuminoids From Glucose. Biotechnology journal, 13(5), 1700576.
13. Grand View Research (2016). Recombinant DNA Technology Market Analysis By Product (Therapeutic Agent, Vaccine, Biotech Crops, Specialty Chemicals), By Component, By Application, By End-use, And Segment Forecasts, 2018-2025 (GVR-1-68038-872-5). Retrieved from www.grandviewresearch.com.
14. Sanchez-Garcia, L., Martin, L., Mangues, R., Ferrer-Miralles, N., Vázquez, E., & Villaverde, A. (2016). Recombinant pharmaceuticals from microbial cells: a 2015 update. Microbial cell factories, 15(1), 33.
15. Rodrigues, J. L., Araujo, R. G., Prather, K. L. J., Kluskens, L. D., Rodrigues, L. R. (2015) Production of curcuminoids from tyrosine by a metabolically engineered *Escherichia coli* using caffeic acid as an intermediate, Biotechnology Journal, 10: 599-U315.
16. Aggarwal, B. B., Harikumar, K. B. (2009) Potential therapeutic effects of curcumin, the anti-inflammatory agent, against neurodegenerative, cardiovascular, pulmonary, metabolic, autoimmune and neoplastic diseases, International Journal of Biochemistry & Cell Biology, 41: 40-59.
17. Maheshwari, R. K., Singh, A. K., Gaddipati, J., Srimal, R. C. (2006) Multiple biological activities of curcumin: A short review, Life Sciences, 78: 2081-2087.
18. Kunnumakkara, A. B., Bordoloi, D., Padmavathi, G., Monisha, J., Roy, N. K., et al. (2017) Curcumin, the golden nutraceutical: multitargeting for multiple chronic diseases, British Journal of Pharmacology, 174: 1325-1348.
19. Shanmugam, M. K., Rane, G., Kanchi, M. M., Arfuso, F., Chinnathambi, A., et al. (2015) The Multifaceted Role of Curcumin in Cancer Prevention and Treatment, Molecules, 20: 2728-2769.
20. Anand, P., Kunnumakkara, A. B., Newman, R. A., Aggarwal, B. B. (2007) Bioavailability of curcumin: Problems and promises, Mol. Pharm., 4: 807-818.
21. Aggarwal, B. B., Ichikawa, H., Garodia, P., Weerasinghe, P., Sethi, G., et al. (2006) From traditional Ayurvedic medicine to modern medicine: identification of therapeutic targets for suppression of inflammation and cancer, Expert Opinion on Therapeutic Targets, 10: 87-118.
22. Vogel, H. A., Pelletier, J. (1815) Curcumin-biological and medicinal properties., J. Pharmacol., 2: 50.
23. Milobedeska, J., Kostanecki, S., Lampe, V. (1910) Structure of curcumin., Ber. Dtsch. Chem. Ges., 43: 2163-2170.
24. Lampe, V., Milobedeska, J. (1913) Studien uber curcumin., Ber. Dtsch. Chem. Ges., 46: 2235-2240.

25. Aggarwal, B. B., Gupta, S. C., Sung, B. (2013) Curcumin: an orally bioavailable blocker of TNF and other pro-inflammatory biomarkers, British Journal of Pharmacology, 169: 1672-1692.
26. Srivastava, R., Dikshit, M., Srimal, R. C., Dhawan, B. N. (1985) ANTI-THROMBOTIC EFFECT OF CURCUMIN, Thrombosis Research, 40: 413-417.
27. Chen, A., Xu, J., Johnson, A. C. (2006) Curcumin inhibits human colon cancer cell growth by suppressing gene expression of epidermal growth factor receptor through reducing the activity of the transcription factor Egr-1, Oncogene, 25: 278-287.
28. Chen, J., Tang, X. Q., Zhi, J. L., Cui, Y., Yu, H. M., et al. (2006) Curcumin protects PC12 cells against 1-methyl-4-phenylpyridinium ion-induced apoptosis by Bcl-2-mitochondria-ROS-iNOS pathway, Apoptosis, 11: 943-953.
29. Divya, C. S., Pillai, M. R. (2006) Antitumor action of curcumin in human papillomavirus associated cells involves downregulation of viral oncogenes, prevention of NFKB and AP-1 translocation and modulation of apoptosis, Molecular Carcinogenesis, 45: 320-332.
30. Kocaadam, B., Sanlier, N. (2017) Curcumin, an active component of turmeric (*Curcuma longa*), and its effects on health, Critical Reviews in Food Science and Nutrition, 57: 2889-2895.
31. Shishodia, S., Chaturvedi, M. M., Aggarwal, B. B. (2007) Role of curcumin in cancer therapy, Current Problems in Cancer, 31: 243-305.
32. Shishodia, S., Singh, T., Chaturvedi, M. M., Modulation of transcription factors by curcumin, in: Aggarwal, B. B., Surh, Y. J., Shishodia, S. (Eds.) Molecular Targets and Therapeutic Uses of Curcumin in Health and Disease, 2007, pp. 127-148.
33. Wang, Z. W., Zhang, Y. X., Banerjee, S., Li, Y. W., Sarkar, F. H. (2006) Notch-1 downregulation by curcumin is associated with the inhibition of cell growth and the induction of apoptosis in pancreatic cancer cells, Cancer, 106: 2503-2513.
34. Bharti, A. C., Donato, N., Aggarwal, B. B. (2003) Curcurnin (diferuloylmethane) inhibits constitutive and IL-6-inducible STAT3 phosphorylation in human multiple myeloma cells, Journal of Immunology, 171: 3863-3871.
35. Dhandapani, K. M., Mahesh, V. B., Brann, D. W. (2007) Curcumin suppresses growth and chemoresistance of human glioblastoma cells via AP-1 and NF kappa B transcription factors, Journal of Neurochemistry, 102: 522-538.
36. Polytarchou, C., Hatziapostolou, M., Papadimitriou, E. (2005) Hydrogen peroxide stimulates proliferation and migration of human prostate cancer cells through activation of activator protein-1 and up-regulation of the heparin affin regulatory peptide gene, J. Biol. Chem., 280: 40428-40435.
37. Leow, P. C., Tian, Q. A., Ong, Z. Y., Yang, Z., Ee, P. L. R. (2010) Antitumor activity of natural compounds, curcumin and PKF 118-310, as Wnt/beta-catenin antagonists against human osteosarcoma cells, Investigational New Drugs, 28: 766-782.
38. Chen, A. P., Xu, J. Y. (2005) Activation of PPAR gamma by curcumin inhibits Moser cell growth and mediates suppression of gene expression of cyclin D1 and EGFR, American Journal of Physiology-Gastrointestinal and Liver Physiology, 288: G447-G456.
39. Zheng, M. Z., Ekmekcioglu, S., Walch, E. T., Tang, C. H., Grimm, E. A. (2004) Inhibition of nuclear factor-kappa B and nitric oxide by curcumin induces G(2)/M cell cycle arrest and apoptosis in human melanoma cells, Melanoma Research, 14: 165-171.
40. Choudhuri, T., Pal, S., Agwarwal, M. L., Das, T., Sa, G. (2002) Curcumin induces apoptosis in human breast cancer cells through p53-dependent Bax induction, Febs Letters, 512: 334-340.
41. Choudhuri, T., Pal, S., Das, T., Sa, G. (2005) Curcumin selectively induces apoptosis in deregulated cyclin D1-expressed cells at G(2) phase of cell cycle in a p53-dependent manner, J. Biol. Chem., 280: 20059-20068.
42. Song, G., Mao, Y. B., Cai, Q. F., Yao, L. M., Ouyang, G. L., et al. (2005) Curcumin induces human HT29 colon adenocarcinoma cell apoptosis by activating p53 and regulating apoptosis-related protein expression, Brazilian Journal of Medical and Biological Research, 38: 1791-1798.
43. Sinha, D., Biswas, J., Sung, B., Aggarwal, B. B., Bishayee, A. (2012) Chemopreventive and Chemotherapeutic Potential of Curcumin in Breast Cancer, Current Drug Targets, 13: 1799-1819.
44. Zlotogorski, A., Dayan, A., Dayan, D., Chaushu, G., Salo, T., et al. (2013) Nutraceuticals as new treatment approaches for oral cancer—I: Curcumin, Oral Oncology, 49: 187-191.
45. Wilken, R., Veena, M. S., Wang, M. B., Srivatsan, E. S. (2011) Curcumin: A review of anti-cancer properties and therapeutic activity in head and neck squamous cell carcinoma, Molecular Cancer, 10.
46. Stan, S. D., Singh, S. V., Brand, R. E. (2010) Chemoprevention strategies for pancreatic cancer, Nature Reviews Gastroenterology & Hepatology, 7: 347-356.
47. Nambiar, D., Singh, R. P. (2013) Advances in Prostate Cancer Chemoprevention: A Translational Perspective, Nutrition and Cancer—an International Journal, 65: 12-25.
48. Sareen, R., Jain, N., Pandit, V. (2013) Curcumin: A Boon to Colonic Diseases, Current Drug Targets, 14: 1210-1218.
49. Aggarwal, B. B., Sung, B. (2009) Pharmacological basis for the role of curcumin in chronic diseases: an age-old spice with modern targets, Trends in Pharmacological Sciences, 30: 85-94.
50. Gupta, S. C., Kim, J. H., Kannappan, R., Reuter, S., Dougherty, P. M., et al. (2011) Role of nuclear factor-kappa B-mediated inflammatory pathways in cancer-related symptoms and their regulation by nutritional agents, Experimental Biology and Medicine, 236: 658-671.
51. Gupta, S. C., Tyagi, A. K., Deshmukh-Taskar, P., Hinojosa, M., Prasad, S., et al. (2014) Downregulation of tumor necrosis factor and other proinflammatory biomarkers by polyphenols, Archives of Biochemistry and Biophysics, 559: 91-99.
52. Chan, M. M. Y., Huang, H. I., Fenton, M. R., Fong, D. (1998) In vivo inhibition of nitric oxide synthase gene expression by curcumin, a cancer preventive natural product with anti-inflammatory properties, Biochemical Pharmacology, 55: 1955-1962.
53. Murakami, A., Furukawa, I., Miyamoto, S., Tanaka, T., Ohigashi, H. (2013) Curcumin combined with turmerones, essential oil components of turmeric, abolishes inflammation-associated mouse colon carcinogenesis, Biofactors, 39: 221-232.
54. Nelson, K. M., Dahlin, J. L., Bisson, J., Graham, J., Pauli, G. F., et al. (2017) The Essential Medicinal Chemistry of Curcumin, Journal of Medicinal Chemistry, 60: 1620-1637.

55. Tonnesen, H. H., Masson, M., Loftsson, T. (2002) Studies of curcumin and curcuminoids. XXVII. Cyclodextrin complexation: solubility, chemical and photochemical stability, International Journal of Pharmaceutics, 244: 127-135.
56. Fujisawa, S., Atsumi, T., Ishihara, M., Kadoma, Y. (2004) Cytotoxicity, ROS-generation activity and radical-scavenging activity of curcumin and related compounds, Anticancer Research, 24: 563-569.
57. Kasim, N. A., Whitehouse, M., Ramachandran, C., Bermejo, M., Lennernas, H., et al. (2004) Molecular properties of WHO essential drugs and provisional biopharmaceutical classification, Mol. Pharm., 1: 85-96.
58. Mohanty, C., Sahoo, S. K. (2010) The in vitro stability and in vivo pharmacokinetics of curcumin prepared as an aqueous nanoparticulate formulation, Biomaterials, 31: 6597-6611.
59. Marczylo, T. H., Verschoyle, R. D., Cooke, D. N., Morazzoni, P., Steward, W. P., et al. (2007) Comparison of systemic availability of curcumin with that of curcumin formulated with phosphatidylcholine, Cancer Chemotherapy and Pharmacology, 60: 171-177.
60. Holder, G. M., Plummer, J. L., Ryan, A. J. (1978) METABOLISM AND EXCRETION OF CURCUMIN (1,7-BIS-(4-HYDROXY-3-METHOXYPHENYL)-1,6-HEPTADIENE-3,5-DIONE) IN THE RAT, Xenobiotica, 8: 761-768.
61. Mehanny, M., Hathout, R. M., Geneidi, A. S., Mansour, S. (2016) Exploring the use of nanocarrier systems to deliver the magical molecule; Curcumin and its derivatives, J. Controlled Rel., 225: 1-30.
62. Rodrigues, J. L., Prather, K. L. J., Kluskens, L. D., Rodrigues, L. R. (2015) Heterologous Production of Curcuminoids, Microbiology and Molecular Biology Reviews, 79: 39-60.
63. Fang, Z., Jones, J. A., Zhou, J. W., Koffas, M.a. G. (2018) Engineering Escherichia coli Co-Cultures for Production of Curcuminoids From Glucose, Biotechnology Journal, 13.
64. Gupta, P., Jordan, C. T., Mitov, M. I., Butterfield, D. A., Hilt, J. Z., et al. (2016) Controlled curcumin release via conjugation into PBAE nanogels enhances mitochondrial protection against oxidative stress, International Journal of Pharmaceutics, 511: 1012-1021.
65. Kudla, G., Murray, A. W., Tollervey, D., Plotkin, J. B. (2009) Coding-Sequence Determinants of Gene Expression in Escherichia coli, Science, 324: 255-258.
66. Ward, N. J., Buckley, S. M. K., Waddington, S. N., Vandendriessche, T., Chuah, M. K. L., et al. (2011) Codon optimization of human factor VIII cDNAs leads to high-level expression, Blood, 117: 798-807.
67. Gustafsson, C., Govindarajan, S., Minshull, J. (2004) Codon bias and heterologous protein expression, Trends in Biotechnology, 22: 346-353.
68. Villalobos, A., Ness, J. E., Gustafsson, C., Minshull, J., Govindarajan, S. (2006) Gene Designer: a synthetic biology tool for constructing artificial DNA segments, Bmc Bioinformatics, 7.
69. Burgess-Brown, N. A., Sharma, S., Sobott, F., Loenarz, C., Oppermann, U., et al. (2008) Codon optimization can improve expression of human genes in Escherichia coli: A multi-gene study, Protein Expression and Purification, 59: 94-102.
70. Fath, S., Bauer, A. P., Liss, M., Spriestersbach, A., Maertens, B., et al. (2011) Multiparameter RNA and Codon Optimization: A Standardized Tool to Assess and Enhance Autologous Mammalian Gene Expression, PLOS ONE, 6.
71. Mauro, V. P., Chappell, S. A. (2014) A critical analysis of codon optimization in human therapeutics, Trends in Molecular Medicine, 20: 604-613.
72. Richardson, S. M., Wheelan, S. J., Yarrington, R. M., Boeke, J. D. (2006) GeneDesign: Rapid, automated design of multikilobase synthetic genes, Genome Research, 16: 550-556.
73. Gao, W. T., Rzewski, A., Sun, H. J., Robbins, P. D., Gambotto, A. (2004) UpGene: Application of a web-based DNA codon optimization algorithm, Biotechnology Progress, 20: 443-448.
74. Jayaraj, S., Reid, R., Santi, D. V. (2005) GeMS: an advanced software package for designing synthetic genes, Nucleic Acids Research, 33: 3011-3016.
75. Bode, M., Khor, S., Ye, H. Y., Li, M. H., Ying, J. Y. (2009) TmPrime: fast, flexible oligonucleotide design software for gene synthesis, Nucleic Acids Research, 37: W214-W221.
76. Gaspar, P., Oliveira, J. L., Frommlet, J., Santos, M.a. S., Moura, G. (2012) EuGene: maximizing synthetic gene design for heterologous expression, Bioinformatics, 28: 2683-2684.
77. Fuglsang, A. (2003) Codon optimizer: a freeware tool for codon optimization, Protein Expression and Purification, 31: 247-249.
78. Hatfield, G. W., Roth, D. A. (2007) Optimizing scaleup yield for protein production: Computationally Optimized DNA Assembly (CODA) and Translation Engineering., Biotechnol. Annu. Rev., 13: 27-42.
79. Inouye, S., Sahara-Miura, Y., Sato, J., Suzuki, T. (2015) Codon optimization of genes for efficient protein expression in mammalian cells by selection of only preferred human codons, Protein Expression and Purification, 109: 47-54.
80. Takakura, Y., Katayama, S., Nagata, Y. (2015) High-level expression of tamavidin 2 in human cells by codon-usage optimization, Bioscience Biotechnology and Biochemistry, 79: 610-616.
81. Shabalina, S. A., Spiridonov, N. A., Kashina, A. (2013) Sounds of silence: synonymous nucleotides as a key to biological regulation and complexity, Nucleic Acids Research, 41: 2073-2094.
82. Tsai, C. J., Sauna, Z. E., Kimchi-Sarfaty, C., Ambudkar, S. V., Gottesman, M. M., et al. (2008) Synonymous Mutations and Ribosome Stalling Can Lead to Altered Folding Pathways and Distinct Minima, Journal of Molecular Biology, 383: 281-291.
83. R., H., Sauna, Z. E., Ambudkar, S. V., Gottesman, M. M., Kimchi-Sarfaty, C. (2009) Silent (synonymous) SNPs: should we care about them?, Methods Mol. Biol., 578: 23-39.
84. Sauna, Z. E., Kimchi-Sarfaty, C. (2011) Understanding the contribution of synonymous mutations to human disease, Nature Reviews Genetics, 12: 683-691.
85. Chen, R., Davydov, E. V., Sirota, M., Butte, A. J. (2010) Non-Synonymous and Synonymous Coding SNPs Show Similar Likelihood and Effect Size of Human Disease Association, PLOS ONE, 5.
86. Komar, A. A. (2009) A pause for thought along the co-translational folding pathway, Trends in Biochemical Sciences, 34: 16-24.
87. Rosenblum, G., Chen, C. L., Kaur, J., Cui, X. N., Zhang, H. B., et al. (2013) Quantifying Elongation Rhythm 88. Hu, S. L., Wang, M. R., Cai, G. P., He, M. Y. (2013) Genetic Code-guided Protein Synthesis and Folding in *Escherichia coli*, J. Biol. Chem., 288: 30855-30861.
89. Sander, I. M., Chaney, J. L., Clark, P. L. (2014) Expanding Anfinsen's Principle: Contributions of Synonymous Codon Selection to Rational Protein Design, Journal of the American Chemical Society, 136: 858-861.
90. Katsuyama, Y., Matsuzawa, M., Funa, N., Horinouch, S. (2008) Production of curcuminoids by *Escherichia coli* carrying an artificial biosynthesis pathway, Microbiology-Sgm, 154: 2620-2628.
91. Eggler, A. L., Gay, K. A., Mesecar, A. D. (2008) Molecular mechanisms of natural products in chemoprevention: Induction of cytoprotective enzymes by Nrf2, Molecular Nutrition & Food Research, 52: S84-S94.
92. Balogun, E., Hoque, M., Gong, P. F., Killeen, E., Green, C. J., et al. (2003) Curcurnin activates the haem oxygenase-1 gene via regulation of Nrf2 and the antioxidant-responsive element, Biochem. J., 371: 887-895.
93. Rushworth, S. A., Ogborne, R. M., Charalambos, C. A., O'connell, M. A. (2006) Role of protein kinase C delta in curcumin-induced antioxidant response element-mediated gene expression in human monocytes, Biochemical and Biophysical Research Communications, 341: 1007-1016.
94. Hsieh, H.-L., Yang, C.-M. (2013) Role of Redox Signaling in Neuroinflammation and Neurodegenerative Diseases, Biomed Research International.
95. Maritim, A. C., Sanders, R. A., Watkins, J. B. (2003) Diabetes, oxidative stress, and antioxidants: A review, Journal of Biochemical and Molecular Toxicology, 17: 24-38.
96. Reuter, S., Gupta, S. C., Chaturvedi, M. M., Aggarwal, B. B. (2010) Oxidative stress, inflammation, and cancer How are they linked?, Free Radical Biology and Medicine, 49: 1603-1616.
97. Orrenius, S., Gogvadze, V., Zhivotovsky, B., Mitochondrial oxidative stress: Implications for cell death, in: Annual Review of Pharmacology and Toxicology, 2007, pp. 143-183.
98. Fariss, M. W., Chan, C. B., Patel, M., Van Houten, B., Orrenius, S. (2005) Defining mitochondrial targets to combat the pleiotropic effects of toxic oxidative stress, Molecular Interventions, 5: 94-111.
99. Wattamwar, P. P., Biswal, D., Cochran, D. B., Lyvers, A. C., Eitel, R. E., et al. (2012) Synthesis and characterization of poly(antioxidant beta-amino esters) for controlled release of polyphenolic antioxidants, Acta Biomaterialia, 8: 2529-2537.
100. Huang, D., Ou, B., Prior, R. L. (2005) The Chemistry behind Antioxidant Capacity Assays, Journal of Agricultural and Food Chemistry, 53: 1841-1856.
101. Rajneesh, Pathak, J., Chatterjee, A., Singh, S. P., Sinha, R. P. (2017) Detection of Reactive Oxygen Species (ROS) in Cyanobacteria Using the Oxidant-sensing Probe 2',7'-Dichlorodihydrofluorescein Diacetate (DCFH-DA), Bio-protocol, 7: e2545.
102. Vomhof-Dekrey, E. E., Picklo, M. J. (2012) The Nrf2-antioxidant response element pathway: a target for regulating energy metabolism, Journal of Nutritional Biochemistry, 23: 1201-1206.
103. Nguyen, T., Nioi, P., Pickett, C. B. (2009) The Nrf2-Antioxidant Response Element Signaling Pathway and Its Activation by Oxidative Stress, J. Biol. Chem., 284: 13291-13295.
104. Chen, Q., Vazquez, E. J., Moghaddas, S., Hoppel, C. L., Lesnefsky, E. J. (2003) Production of reactive oxygen species by mitochondria—Central role of complex III, J. Biol. Chem., 278: 36027-36031.
105. Droese, S., Brandt, U., Molecular Mechanisms of Superoxide Production by the Mitochondrial Respiratory Chain, in: Kadenbach, B. (Ed.) Mitochondrial Oxidative Phosphorylation: NuclearEncoded Genes, Enzyme Regulation, and Pathophysiology, 2012, pp. 145-169.
106. Marchi, S., Giorgi, C., Suski, J. M., Agnoletto, C., Bononi, A., et al. (2012) Mitochondria-ROS crosstalk in the control of cell death and aging., J. Signal Transduct., 2012: 17.
107. Madrigal, J. L. M., Olivenza, R., Moro, M. A., Lizasoain, I., Lorenzo, P., et al. (2001) Glutathione depletion, lipid peroxidation and mitochondrial dysfunction are induced by chronic stress in rat brain, Neuropsychopharmacology, 24: 420-429.
108. Zhong, H., Yin, H. (2015) Role of lipid peroxidation derived 4-hydroxynonenal (4-HNE) in cancer: Focusing on mitochondria, Redox Biology, 4: 193-199.
109. Butterfield, D. A., Di Domenico, F., Barone, E. (2014) Elevated risk of type 2 diabetes for development of Alzheimer disease: A key role for oxidative stress in brain, Biochimica Et Biophysica ActaMolecular Basis of Disease, 1842: 1693-1706.
110. Federico, A., Cardaioli, E., Da Pozzo, P., Formichi, P., *Gallus*, G. N., et al. (2012) Mitochondria, oxidative stress and neurodegeneration, Journal of the Neurological Sciences, 322: 254-262.
111. Huang, H.-C., Xu, K., Jiang, Z.-F. (2012) Curcumin-Mediated Neuroprotection Against Amyloid-betaInduced Mitochondrial Dysfunction Involves the Inhibition of GSK-3 beta, Journal of Alzheimers Disease, 32: 981-996.
112. Ichikawa, Y., Ghanefar, M., Bayeva, M., Wu, R., Khechaduri, A., et al. (2014) Cardiotoxicity of doxorubicin is mediated through mitochondrial iron accumulation, J. Clin. Invest., 124: 617-630.
113. Rolo, A. P., Palmeira, C. M. (2006) Diabetes and mitochondrial function: Role of hyperglycemia and oxidative stress, Toxicology and Applied Pharmacology, 212: 167-178.
114. Victor, V. M., Apostolova, N., Herance, R., Hernandez-Mijares, A., Rocha, M. (2009) Oxidative Stress and Mitochondrial Dysfunction in Atherosclerosis: Mitochondria-Targeted Antioxidants as Potential Therapy, Current Medicinal Chemistry, 16: 4654-4667.
115. Sandur, S. K., Pandey, M. K., Sung, B., Ahn, K. S., Murakatni, A., et al. (2007) Curcumin, demethtoxycurcumin, bisdemethoxycurcumin, tetrahydrocurcumin and turmerones differentially regulate anti-inflammatory and anti-proliferative responses through a ROS-independent mechanism, Carcinogenesis, 28: 1765-1773.
116. Shukla, S., Zaher, H., Hartz, A., Bauer, B., Ware, J. A., et al. (2009) Curcumin Inhibits the Activity of ABCG2/BCRP1, a Multidrug Resistance-Linked ABC Drug Transporter in Mice, Pharm. Res., 26: 480-487.
117. Zhang, W. X., Tan, T. M. C., Lim, L. Y. (2007) Impact of curcumin-induced changes in P-glycoprotein and CYP3A expression on the pharmacokinetics of peroral celiprolol and Midazolam in rats, Drug Metabolism and Disposition, 35: 110-115.
118. Fan, H. J., Liang, Y., Jiang, B., Li, X. B., Xun, H., et al. (2016) Curcumin inhibits intracellular fatty acid synthase and induces apoptosis in human breast cancer MDA-MB-231 cells, Oncology Reports, 35: 2651-2656.

119. Sonis, S. T. (2011) Oral mucositis, Anti-Cancer Drugs, 22: 607-612.
120. Saadeh, C. E. (2005) Chemotherapy- and radiotherapy-induced oral mucositis: Review of preventive strategies and treatment, Pharmacotherapy, 25: 540-554.
121. Raber-Durlacher, J. E., Elad, S., Barasch, A. (2010) Oral mucositis, Oral Oncology, 46: 452-456.
122. Donnelly, J. P., Bellm, L. A., Epstein, J. B., Sonis, S. T., Symonds, R. P. (2003) Antimicrobial therapy to prevent or treat oral mucositis, Lancet Infectious Diseases, 3: 405-412.
123. Saunders, D. P., Epstein, J. B., Elad, S., Allemano, J., Bossi, P., et al. (2015) Systematic review of antimicrobials, mucosal coating agents, anesthetics, and analgesics for the management of oral mucositis in cancer patients (vol 21, pg 3191, 2013), Supportive Care in Cancer, 23: 601-602.
124. Nicolatou-Galitis, O., Sarri, T., Bowen, J., Di Palma, M., Kouloulias, V. E., et al. (2013) Systematic review of anti-inflammatory agents for the management of oral mucositis in cancer patients, Supportive Care in Cancer, 21: 3179-3189.
125. Sonis, S. T. (2007) Pathobiology of oral mucositis: novel insights and opportunities., J. Supportive Oncol., 5: 3-11.
126. Scully, C., Epstein, J., Sonis, S. (2003) Oral mucositis: A challenging complication of radiotherapy, chemotherapy, and radiochemotherapy: Part 1, pathogenesis and prophylaxis of mucositis, Head and Neck-Journal for the Sciences and Specialties of the Head and Neck, 25: 1057-1070.
127. Sonis, S. T. (2004) The pathobiology of mucositis, Nature Reviews Cancer, 4: 277-284.
128. Sonis, S. L. (2002) The biologic role for nuclear factor-kappaB in disease and its potential involvement in mucosal injury associated with anti-neoplastic therapy, Critical Reviews in Oral Biology & Medicine, 13: 380-389.
129. Hwang, D., Popat, R., Bragdon, C., O'donnell, K. E., Sonis, S. T. (2005) Effects of ceramide inhibition on experimental radiation-induced oral mucositis, Oral Surgery Oral Medicine Oral Pathology Oral Radiology and Endodontics, 100: 321-329.
130. Blijlevens, N. M. A., Donnelly, J. P., De Pauw, B. E. (2000) Mucosal barrier injury: biology, pathology, clinical counterparts and consequences of intensive treatment for haematological malignancy: an overview, Bone Marrow Transplantation, 25: 1269-1278.
131. Rezvani, M., Ross, G. A. (2004) Modification of radiation-induced acute oral mucositis in the rat, International Journal of Radiation Biology, 80: 177-182.
132. Van't Land, B., Blijlevens, N. M. A., Marteijn, J., Timal, S., Donnelly, J. P., et al. (2004) Role of curcumin and the inhibition of NF-kappa B in the onset of chemotherapy-induced mucosal barrier injury, Leukemia, 18: 276-284.
133. Elad, S., Meidan, I., Sellam, G., Simaan, S., Zeevi, I., et al. (2013) Topical Curcumin for the Prevention of Oral Mucositis in Pediatric Patients: Case Series, Alternative Therapies in Health and Medicine, 19: 21-24.
134. Sonis, S. T., Tracey, C., Shklar, G., Jenson, J., Florine, D. (1990) An animal-model for mucositis induced by cancer-chemotherapy., Oral Surgery Oral Medicine Oral Pathology Oral Radiology and Endodontics, 69: 437-443.
135. Watanabe, S., Suemaru, K., Nakanishi, M., Nakajima, N., Tanaka, M., et al. (2014) Assessment of the hamster cheek pouch as a model for radiation-induced oral mucositis, and evaluation of the protective effects of keratinocyte growth factor using this model, International Journal of Radiation Biology, 90: 884-891.
136. Viet, C. T., Corby, P. M., Akinwande, A., Schmidt, B. L. (2014) Review of Preclinical Studies on Treatment of Mucositis and Associated Pain, Journal of Dental Research, 93: 868-875.
137. Tao, K., Fang, M., Alroy, J., Sahagian, G. G. (2008) Imagable 4T1 model for the study of late stage breast cancer, BMC Cancer, 8.
138. Aslakson, C. J., Miller, F. R. (1992) Selective Events in the Metastatic Process Defined by Analysis of the Sequential Dissemination of Subpopulations of a Mouse Mammary Tumor, Cancer Research, 52: 1399-1405.
139. Lelekakis, M., Moseley, J., Martin, T. J., Hards, D., Williams, E., et al. (1999) A novel orthotopic model of breast cancer metastasis to bone, Clin Exp Metastasis, 17: 163-170.
140. Poust, S., Hagen, A., Katz, L., Keasling, J. D. (2014) Narrowing the gap between the promise and reality of polyketide synthases as a synthetic biology platform, Current Opinion in Biotechnology, 30: 32-39.
141. Paddon, C. J., Keasling, J. D. (2014) Semi-synthetic artemisinin: a model for the use of synthetic biology in pharmaceutical development, Nature Reviews Microbiology, 12: 355-367.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of making a curcuminoid in a mammalian cell, the method comprising:
   expressing enzymes 4-coumaroyl-CoA ligase (4CL1) and one of 1) curcuminoid synthase (CUS) and 2) curcumin synthase (CURS1) and diketide-CoA synthase (DCS) in the mammalian cell, and optionally further expressing in the mammalian cell one or more additional enzymes selected from the group consisting of tyrosine ammonia lyase (TAL), DCS, CURS1, 4 coumarate 3-hydroxylase (C3H), caffeoyl-CoA 3-O-methyltransferase (CCoAOMT), and acetyl-CoA carboxylase (ACC); and
   contacting the mammalian cell expressing the enzymes with a starting material being tyrosine, ferulic acid or p-coumaric acid to convert the starting material to the curcuminoid.

2. The method of claim 1, wherein the starting material is ferulic acid.

3. The method of claim 2, wherein the curcuminoid is curcumin, demethoxycurcumin, or a combination thereof.

4. The method of claim 1, wherein the starting material is tyrosine.

5. The method of claim 4, wherein the enzymes comprise TAL, 4CL1, and CUS.

6. The method of claim 5, wherein the curcuminoid is bisdemethoxycurcumin.

7. The method of claim 4, wherein the enzymes comprise TAL, C3H, 4CL1, CCoAOMT, and CUS or CURS1 and DCS.

8. The method of claim 7, wherein the enzymes comprise TAL, C3H, 4CL1, CCoAOMT, and CUS.

9. The method of claim 7, wherein the enzymes comprise TAL, C3H, 4CL1, CCoAOMT, CURS1, and DCS.

10. The method of claim 7, wherein the curcuminoid is one or more of curcumin, demethoxycurcumin, and bisdemethoxycurcumin.

11. The method of claim 1, further comprising, prior to expressing the enzymes, delivering genetic material encoding the enzymes to the mammalian cell.

12. The method of claim 11, wherein delivering the genetic material is via polymer-DNA, a viral system, or clustered regularly interspaced short palindromic repeats (CRISPR)/CRISPR-associated protein-9 (Cas9) system.

13. The method of claim 12, wherein the polymer-DNA delivery includes modified polyethylenimine (PEI) polymer.

14. The method of claim 12, wherein the CRISPR/Cas9 system includes simultaneous insertion of up to six genes at a single locus.

15. The method of claim 11, wherein delivering the genetic material includes delivering a different concentration of genetic material for each of the enzymes.

16. The method of claim 1, further comprising providing malonyl-CoA to the cell.

17. The method of claim 16, wherein providing the malonyl-CoA to the cell includes expressing ACC in the cell.

18. A method of making a curcuminoid in a mammalian cell, the method comprising:
   introducing ferulic acid to the mammalian cell, and performing one of the following:
   (a) expressing 4-coumaroyl-CoA ligase (4CL1) and curcuminoid synthase (CUS) in the mammalian cell;
   (b) expressing tyrosine ammonia lyase (TAL), 4CL1, and CUS in the mammalian cell;
   (c) expressing TAL, 4CL1, CUS, 4-coumarate 3-hydroxylase (C3H), and caffeoyl-CoA 3-0-methyltransferase (CCoAOMT) in the mammalian cell; or
   (d) expressing TAL, 4CL1, C3H, CCoAOMT, curcumin synthase (CURS 1), and diketide-CoA synthase (DCS) in the mammalian cell;
   wherein the expressing the enzymes converts ferulic acid to the curcuminoid.

19. The method of claim 18, wherein the method further comprises expressing acetyl-CoA carboxylase (ACC) in the mammalian cell.

* * * * *